(12) United States Patent
Nadkarni et al.

(10) Patent No.: US 7,081,360 B2
(45) Date of Patent: Jul. 25, 2006

(54) EXPRESSION OF G PROTEIN-COUPLED RECEPTORS WITH ALTERED LIGAND BINDING AND/OR COUPLING PROPERTIES

(75) Inventors: Anupama K. Nadkarni, River Edge, NJ (US); Joshua Trueheart, Concord, MA (US)

(73) Assignee: Cadus Technologies, Inc., New York, NY (US)

( * ) Notice: Subject to any disclaimer, the term of this patent is extended or adjusted under 35 U.S.C. 154(b) by 50 days.

(21) Appl. No.: 09/362,286

(22) Filed: Jul. 27, 1999

(65) Prior Publication Data

US 2002/0197706 A1 Dec. 26, 2002

Related U.S. Application Data

(60) Provisional application No. 60/094,451, filed on Jul. 28, 1998.

(51) Int. Cl.
C12N 1/19 (2006.01)
C07K 14/705 (2006.01)

(52) U.S. Cl. ............... 435/254.21; 435/366; 435/361; 435/69.1; 435/320.1; 530/350; 536/23.5

(58) Field of Classification Search ............ 530/350; 435/325, 254.11, 69.1, 320.1
See application file for complete search history.

(56) References Cited

U.S. PATENT DOCUMENTS

| | | | | |
|---|---|---|---|---|
| 4,948,874 | A | 8/1990 | Kronvall et al. | 530/350 |
| 5,096,815 | A | 3/1992 | Ladner et al. | 435/69.1 |
| 5,401,629 | A | 3/1995 | Harpold et al. | 435/6 |
| 5,436,128 | A | 7/1995 | Harpold et al. | 435/6 |
| 5,482,835 | A | 1/1996 | King et al. | 435/6 |
| 5,576,210 | A | 11/1996 | Sledziewski et al. | 435/254.21 |
| 5,618,676 | A * | 4/1997 | Hitzeman et al. | 435/69.1 |
| 5,691,188 | A | 11/1997 | Pausch et al. | 435/254 |
| 5,739,029 | A | 4/1998 | King et al. | 435/254.21 |

FOREIGN PATENT DOCUMENTS

| | | |
|---|---|---|
| EP | 568925 | 11/1993 |
| EP | 0711830 * | 5/1996 |
| EP | 344024 | 8/1996 |
| WO | WO 8810308 | 12/1988 |
| WO | WO 9112273 | 8/1991 |
| WO | WO 9205244 | 4/1992 |
| WO | WO 9208740 | 5/1992 |
| WO | WO 92/18641 * | 10/1992 |
| WO | WO 9310230 | 5/1993 |
| WO | WO 9423025 | 10/1994 |
| WO | WO 9530012 | 11/1995 |
| WO | WO 96/18651 * | 6/1996 |
| WO | WO 9711159 | 3/1997 |
| WO | WO 9813513 | 4/1998 |

OTHER PUBLICATIONS

Mikayama T. Molecular cloning and functional expression of a cDNA encoding glycosylation-inhibiting factor. Proc. Natl. Acad. Sci. USA vol. 90, pp. 10056-10060, 1993.*
Voet et al. Biochemistry. 1990. John Wiley & Sons, Inc.. pp. 126-128 and 228-234.*
Bowie et al. Deciphering the Message in Protein Sequences: Tolerance to Amino Acid Substitutions. Science. vol. 247, pp. 1306-1310, 1990.*
Gether U. Uncovering molecular mechanisms involved in activation of G protein-coupled receptors. Endocr Rev. Feb. 2000;21(1):90-113.*
Yan et al., Two-amino acid molecular switch in an epithelial morphogen that regulates binding to two distinct receptors. Science 290: 523-527, 2000.*
R;Kluxen, F.W.; Bruns, C.; Lubbert, H. Proc. Natl. Acad. Sci. U.S.A. 89, 4618-4622, 1992.*

(Continued)

*Primary Examiner*—Eileen B. O'Hara
(74) *Attorney, Agent, or Firm*—Edwards Angell Palmer & Dodge LLP; Peter C. Lauro, Esq.

(57) ABSTRACT

Modified forms of G protein-coupled receptors which display altered ligand binding and/or coupling properties are provided as well as cells expressing such receptors and assays utilizing these cells for screening and identifying pharmaceutically effective compounds that specifically modulate the activity of a these modified forms of G protein coupled receptors. Yeast or mammalian cells can be used to express such receptors. The subject assays enable rapid screening of large numbers of compounds (e.g., compounds in a library) to identify those which are receptor agonists or antagonists. Compositions of matter, such as these novel receptors, novel recombinant yeast cells and novel gene constructs, are also provided. The instant assays provide a convenient format for discovering compounds which can be useful in modulating cellular function, as well as in understanding the pharmacology of compounds that specifically interact with these modified forms G protein coupled receptors.

18 Claims, 9 Drawing Sheets

OTHER PUBLICATIONS

Alison, Malcolm R. et al. "Growth factors and growth factor receptors," *Brit. J. of Hosp. Med.* 49(11):774-788 (1993).

Altieri, Dario C. "Proteases and protease receptors in modulation of leukocyte effector functions," *Journal of Leukocyte Biology* 58:120-127 (Aug. 1995).

Arkinstall, Steve, et al., "Co-expression of the neurokinin NK2 receptor and G-protein components in the fission yeast *Schizosaccharomyces pombe,*" *FEBS Letters* 375:183-187 (1995).

Belka, C. et al. "The role of tyrosine kinases and their substrates in signal transmission of hematopoietic growth factors: a short review," *Leukemia* 9:754-761 (1995).

Bender, Alan and Sprague, George F. Jr. "Pheromones and Pheromone Receptors Are the Primary Determinants of Mating Specificity in the Yeast *Saccharomyces cerevisiae,*" *Genetics* 121:463-476 (Mar. 1989).

Birnbaumer, Lutz "Transduction of receptor signal into modulation of effector activity by G proteins: the first 20 years or so . . . ," *FASEB Journal* 4:3178-3188 (1990).

Blinder, Dmitry et al. "Constitutive Mutants in the Yeast Pheromone Response: Ordered Function of the Gene Products," *Cell* 56:479-486 (Feb. 1989).

Brennan, Fionula M. et al. "Detection of interleukin 8 biological activity in synovial fluids from patients with rheumatoid arthritis and production of interleukin 8 mRNA by isolated synovial cells" *Eur. J. Immunol.* 20:2141-2144 (1990).

Chambers, D. A. et al. "Neuroimmune Modulation: Signal Tranduction and Catecholamines," *Neurochem. Int.* 22(2):95-110 (1993).

Chan, Russell K. and Otte, Carol A. "Isolation and Genetic Analysis of *Saccharomyces cerevisiae* Mutants Supersensitive to G1 Arrest by a Factor and α Factor," *Molecular and Cellular Biol.* 2(1):11-20 (Jan. 1982).

Conklin, Bruce R. et al. "Substitution of three amino acids switches receptor specificity of $G_{qa}$ to that of $G_{ia1}$" *Nature* 363:274-276 (May 1993).

Coria, Roberto, et al. "Separate Roles for N- and C-Termini of the STE4 (β) Subunit of the *Saccharomyces cerevisiae* G Protein in the Mediation of the Growth Arrest. Lack of Growth-Arresting Activity of Mammalian βγ Complexes," *Yeast* 12:41-51 (1996).

Coria, Roberto, et al. "STE2/SCG1-dependent inhibition of STE4-induced growth arrest by mutant STE4$^{\Delta C6}$ in the yeast pheromone response pathway," *FEBS Letters* 367:122-126 (1995).

Dietzel, et al., "The Yeast SCG1 Gene: A Gα-like Protein Implicated in the a- and α-Factor Response Pathway", Cell, vol. 50, pp. 1001-1010, (1987).

Dubois, Patrice M. et al. "Role of the transmembrane and cytoplasmic domains of surface IgM in endocytosis and signal transduction," *Eur. J. Immunol.* 22:851-857 (1992).

Etienne, Gilles et al. "A Screening Method for Antifungal Substances Using *Saccharomyces cerevisiae* Strains Resistant to Polyene Macrolides," *The Journal of Antibiotics* 43(2):199-206 (Feb. 1990).

Funaro, Ada et al. "Human CD38 is associated to distinct molecules which mediate transmembrane signaling in different lineages," *Eur. J. Immunol.* 23:2407-2411 (1993).

Gordon, John "B-cell signalling via the C-type lectins CD23 and CD72," *Immunology Today* 15(9):411-417 (1994).

Gotlieb, Alice B. et al. "Detection of a γ Intefeon-Induced Protein IP-10 in Psoriatic Plaques" *J. Exp. Med.* 168:941-948 (Sep. 1988).

Gros, Philippe et al. "Mammalian Multidrug Resistence Gene: Complete cDNA Sequence Indicates Strong Homology to Bacterial Transport Proteins," *Cell* 47:371-380 (Nov. 1986).

Hagen, David C. et al. "Evidence the yeast STE3 gene encodes a receptor for the peptide pheromone a factor: Gene sequence and implications for the structure of the presumed receptor," *Proc. Natl. Acad. Sci. USA* 83:1418-1422 (Mar. 1986).

Hartwell, Leland H. "Mutants of *Saccharomyces cerevisiae* Unresponsive to Cell Division Control by Polypeptide Mating Hormone," *J. Cell Biol.* 85:811-822 (Jun. 1980).

Hechtman, D.H. et al. "Intravenous Endothelial Interleukin-8 Reduces Neurotrophil Accumulation at Intradermal Sites of Inflammation" *FASEB J.* 4(4):A890, Abtr. 3618 (Feb. 1990).

Holmes, William E. et al. "Structure and Functional Expression of a Human Interleukin-8 Receptor" *Science* 253:1278-1280 (Sep. 1991).

Huang, Hao-jen et al. "Functional Expression of RAT M5 Muscarinic Acetylcholine Receptor In Yeast" *Biochemical and Biophysical Research Communications* 182(3):1180-1186 (Feb. 1992).

Jakobs, K. H. et al. "Dual regulation of adenylate cyclase. A signal tranduction mechanism of membrane receptors," *Basic Res. Cardiol.* 81:1-9 (1986).

Kajkowski, Eileen et al. "Investigation of Growth Hormone Releasing Hormone Receptor Structure and Activity Using Yeast Expression Technologies" *J. Of Receptor & Signal Transduction Research* 17(1-3):293-303 (1997).

Kang, Yoon-Se et al. "Effects of expression of mammalian galpha and hybrid mammalian yeast galpha proteins on the yeast pheromones response signal transduction pathway," *J. Mol. Biol.* 10(6):2582-2590 (1990).

King, Klim et al. "Control of Yeast Mating Signal Transduction by a Mammalian $\beta_2$-Adrenergic Receptor and $G_s$ α Subunit," *Science* 250:121-123 (Oct. 1990).

Kosugi, Shinji et al. "Characterization of heterogeneous mutations causing constitutive activation of the luteinizing hormone receptor in familial male precocious puberty," *Human Molecular Genetics* 4(2):183-188 (1995).

Kuchler, Karl and Thorner, Jeremy "Functional expression of human *mdr1* in the yeast *Saccharomyces cerevisiae,*" *Proc. Natl. Acad. Sci. USA* 89:2302-2306 (Mar. 1992).

Kuchler, Karl et al. "*Saccharomyces cerevisiae* STE6 gene product: a novel pathway for protein export in eukaryotic cells," *The EMBO Journal.* 8(13):3973-3984 (1989).

Lambright, David G. et al. "Structural determinants for activation of the α-subunit of a heterotrimeric G protein," *Nature* 369:621-628 (Jun. 1994).

Leberer, Ekkehard, et al., "Dominant-negative Mutants of a Yeast G-Protein β Subunit Identify Two Functional Regions Involved in Pheromone Signalling", The EMBO Journal, vol. 11, No. 13, pp. 4805-4813, (1992).

Lee, James et al. "Characterization of Two High Affinity Human Interleukin-8 Receptors" *J. Biol. Chem.* 267(23):16283-16287 (Aug. 1992).

Leonard, Edward J. et al. "Chemotactic Activity and Receptor Binding of Neutrophil Attractant/Activation Protein-1 (NAP-1) and Structurally Related Host Defense Cytokines: Interaction of NAP-2 With the NAP-1 Receptor" *Journal of Leukocyte Biology* 49:258-265 (1991).

Mackay, Vivian and Manney, Thomas R. "Mutations Affecting Sexual Conjugation and Related Processes in *Saccharomyces cerevisiae*. II Genetic Analysis of Nonmating Mutants," *Genetics* 76:273-288 (Feb. 1974).

Milano, C.A. et al. "Enhanced Myocardial Funtion in Transgenic Mice Overexpressing the $\beta_2$-Adrenergic Receptor," *Science* 264:582-586 (Apr. 1994).

Murphy, A.J.M. et al. "Autocrine Stimulation of Yeast through Human G-Coupled Receptors," *J. Cell Biochem.* 18B:224 (1994).

Murphy, Philip M. and Tiffany, H. Lee "Cloning of Complementary DNA Encoding a Functional Human Interleukin-8 Receptor" *Science* 253:1280-1282 (Sep. 1991).

Murphy, Philip and McDermott, David "Functional Expression of the Human Formyl Peptide Receptor in Xenopus Oocytes Requires a Complementary Human Factor" *The Journal of Biological Chemistry* 266(19):12560-12567 (Jul. 1991).

Nakayama, N. et al. "Common signal transduction system, shared by *STE2* and *STE3* in haploid cells of *Saccharomyces cerevisiae*: autocrine cell-cycle arrest results from forced expression of *STE2*," *The EMBO Journal* 6(1):249-254 (1987).

Noelle, Randolph J. et al. "CD40 and its ligand, an essential ligand-receptor pair for thymus-dependent B-cell activation," *Immunol. Today* 13(11):431-433 (1992).

Nye, Jeffrey S. and Kopan, Raphael "Vertebrate ligands for Notch," *Current Biology* 5(9):966-969 (1995).

Oppenheim, Joost J. et al. "Properties of the Novel Proinflammatory Supergene "Intercrine" Cytokine Family" *Annu. Rev. Immunol.* 9:617-648 (1991).

Payette, Paul et al. "Expression and pharmacological characterization of human M1 muscarinic receptor in *saccharomyces cervisiae*," *FEBS Letters* 266(1,2):21-25 (Jun. 1990).

Price, Laura A. et al. "Pharmacological Characerization of the at $A_{2a}$ Adenosine Receptor Functionally Coupled to the Yeast Pheromone Response Pathway" *Molecular Pharmacology* 50:829-837 (1996).

Price, Laura A. et al. "Functional Coupling of a Mammalian Somatostatin Receptor to the Yeast Pheromone Response Pathway," *Molecular and Cellular Biology* 15(11):6188-6195 (Nov. 1995).

Raymond, Martine et al. "Functional Complemetation of Yeast *ste6* by a Mammalian Multidrug Resistence *mdr* Gene," *Science* 256:232-234 (Apr. 1992).

Russell, Marijane et al. "G Protein Amino-Terminal $\alpha_{i2}/\alpha_s$ Chimeras Reveal Amino Acids Important in Regulating $\alpha_s$ Activity," *Molecular Pharmacology* 44:255-263 (1993).

Sander, Peter et al. "Expression of the human $D_{2s}$ dopamine receptor in the yeasts *Saccharomyces cerevisiae* and *Schizosaccharomyces pombe*: a comparative study" *FEBS Letters* 344:41-46 (1994).

Schröder, Jens-Michael and Christophers, Enno "Identification of $C5a_{des\ arg}$ and an Anionic Neutrophil-Activating Peptide (ANAP) in Psoriatic Scales" *J. Invest. Dermatol.* 87:53-58 (1986).

Sticherling, Michael et al. "Localization of Neutrophil-Activating Peptide-1/Interleukin-8-Immunoreactivity in Normal and Psoriatic Skin" *J. Invest. Dermatol.* 96:26-30 (1991).

Sullivan, Kathleen A. et al. "Identification of receptor contact site involved in receptor-G protein coupling," *Nature* 330:758-760 (Dec. 1987).

Talmont, Franck, et al. "Expression and pharmacological characterization of the human µ-opioid receptor in the methylotrophic yeast *Pichia pastoris*," *FEBS Letters* 394:268-272 (1996).

Tate, Christopher et al. "Heterologous expression of G-protein-coupled receptors" *Tib Tech* 14:426-430 (1996).

Teem, John L. et al. "Identification of Revertants for the Cystic Fibrosis ΔF508 Mutation Using STE6-CFTR Chimeras in Yeast," *Cell* 73:335-346 (Apr. 1993).

Thelen, Marcus et al. "Mechanism of neutrophil activation by NAF, a novel monocyte-derived peptide agonist" *FASEB J.* 2:2702-2706 (1998).

Van Zee, Kimberly J. et al. "IL-8 in Septic Shock, Endotoxemia, and After IL-1 Administration" *J. Immunol.* 146(10):3478-3482 (May 1991).

Walz, Alfred et al. "Structure and Neutrophil-activating Properties of a Novel Inflammatory Peptide (ENA-78) with Homology to Interleukin 8" *J. Exp. Med.* 174:1355-1362 (Dec. 1991).

Weiss, H. Markus et al. "Expression of functional mouse 5-$HT_{5A}$ serotonin receptor in the methylotrophic yeast *Pichia pastoris*: pharmacological characterization and localization" *FEBS Letters* 377:451-456 (1995).

Whiteway, Malcom S. et al. "Association of the Yeast Pheromone Response G Protein βγ Subunits with the MAP Kinase Scaffold Ste5p" *Science* 269:1572-1575 (Sep. 1995).

Whiteway, Malcolm S. et al. "Genetic Identification of Residues Involved in Association of α and βG-Protein Subunits" *Molecular and Cellular Biology* 14(5):3223-3229 (1994).

Whiteway, Malcolm S. et al. "Mutagenesis of Ste18, a putative Gγ subunit in the *Saccharomyces cerevisiae* pheromone response pathway" *Biochem. Cell. Biol.* 70: 1232-1237 (1992).

* cited by examiner

Ligand minus

IL8

GRO@MGSA

NAP-2

PTx sensitivity of rIL8Ar variants

FIG. 9

EXPRESSION OF G PROTEIN-COUPLED RECEPTORS WITH ALTERED LIGAND BINDING AND/OR COUPLING PROPERTIES

RELATED APPLICATION

This application has been converted from U.S. provisional patent application Ser. No. 60/094,451, filed Jul. 28, 1998, which is incorporated herein, in its entirety, by reference.

BACKGROUND OF THE INVENTION

Cell surface receptors are an important class of proteins involved in cellular functioning because they are the primary mediators of cell to cell communication. In particular, G protein-coupled receptors (GPCRs) are an important category of cell surface receptors. The medical importance of these receptors is evidenced by the fact that more than 60% of all commercially available prescription drugs work by interacting with known GPCRs.

In their resting state, the G proteins, which consist of alpha ($\alpha$), beta ($\beta$) and gamma ($\gamma$) subunits, are complexed with the nucleotide guanosine diphosphate (GDP) and are in contact with the receptors to which they are coupled. When a hormone or other first messenger binds to receptor, the receptor changes conformation and this alters its interaction with the G protein. This spurs the $\alpha$ subunit to release GDP, and the more abundant nucleotide guanosine triphosphate (GTP) replaces it, activating the G protein. The G protein then dissociates to separate the $\alpha$ subunit from the still complexed beta and gamma subunits. Either the G$\alpha$ subunit, or the G$\beta\gamma$ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the G$\alpha$ converts the GTP to GDP, thereby inactivating itself. The inactivated G$\alpha$ may then reassociate with the G$\beta\gamma$ complex.

Hundreds, if not thousands, of receptors convey messages through heterotrimeric G proteins, of which at least 17 distinct G$\alpha$ subunit forms have been isolated. Most G protein-coupled receptors are comprised of a single protein chain that is threaded through the plasma membrane seven times. Such receptors are often referred to as seven-transmembrane domain receptors (STRs). More than a hundred different GPCRs have been found, including many distinct receptors that bind the same ligand, and there are likely many more GPCRs awaiting discovery.

The mating factor receptors of yeast cells (STE2 and STE3) span the membrane of the yeast cell seven times and are coupled to yeast G proteins. Heterologous GPCRs can be expressed in yeast cells and can be made to couple to yeast G proteins resulting in the transduction of signals via the endogenous yeast pheromone system signaling pathway which is normally activated by STE2 or STE3. In some cases, such heterologous receptors can be made to couple more effectively to the yeast pheromone system signaling pathway by coexpressing a heterologous G protein $\alpha$ subunit (e.g. U.S. Pat. No. 5,482,835 to King et al), by expressing a chimeric G protein subunit (e.g. WO 94/23025), or by expressing a chimeric G protein-coupled receptor (e.g., U.S. Pat. No. 5,576,210 issued to Sledziewski et al.).

The $\beta\gamma$ subunits of the activated G protein stimulate the downstream elements of the pheromone response pathway, including the Ste20p protein kinase, and a set of kinases that are similar to MEK kinase, MEK (MAP kinase kinase), and MAP kinase of mammalian cells and are encoded by the STE11, STE7, and FUS3/KSS1 genes, respectively (Whiteway et al. 1995. Science. 269:1572).

Members of the family of chemotactic cytokines, which have been proposed to be named "chemokines" for short, are being identified as vital initiators and promulgators of inflammatory and immunological reactions (Oppenheim et al. (1991) *Annu Rev Immunol* 9:617). The chemokines range from 8 to 11 kD in MW, are active over a 1 to 100-ng/ml concentration range, and are produced by a wide variety of cell types. They are induced by exogenous irritants and endogenous mediators such as IL-1, TNF, PDGF, and IFN-$\gamma$. The chemokines bind to specific cell surface receptors with a $K_D$ of 0.4 to 4 nM. These chemokines can be considered "second-order" cytokines that appear to be less pleiotropic than "first-order" proinflammatory cytokines because they are not potent inducers of other cytokines and exhibit more specialized functions in inflammation and repair. As shown in Table 1, some of the chemokines have been assigned to a "chemokine $\alpha$" subset based on their gene cluster on chromosome 4 (q12–21) and based on the fact that the first two of their four cysteine groups are separated by one amino acid (C—X—C).

TABLE 1

Properties of the chemokine $\alpha$ subfamily

| Cytokine | Cell sources | Exogenous stimulants | Endogenous inducers | Chemotactic or haptotactic responses | Major activities |
|---|---|---|---|---|---|
| IL-9 | Monocytes Neutrophils Fibroblasts Endothelial cells Keratinocytes Large granular lymphs T lymphocytes | Endotoxin Mitogens Particulates Viruses | IL-1 TNF IFN-$\gamma$ costimulant IL-3 | Neutrophils Basophils Unstimulated T cells Melanoma Cells | Activates PMN ↑ Neutrophil adhesion ↓ Basophil histamine ↑ Keratinocyte growth Acute Inflammation |
| GRO-$\alpha\beta\gamma$/ mu/KC muMIP-2$\alpha\beta$ | Monocytes Fibroblasts Endothelial cells | Endotoxin | IL-1 TNF | Neutrophils | Degranulates PMN ↑ Melanoma cell growth ↑ Fibroblast growth Acute inflammation |

TABLE 1-continued

Properties of the chemokine α subfamily

| Cytokine | Cell sources | Exogenous stimulants | Endogenous inducers | Chemotactic or haptotactic responses | Major activities |
|---|---|---|---|---|---|
| CTAP III/ βTG | Monocytes Platelets | Platelet activators | | Fibroblasts | ↑ Fibroblast growth |
| βTG/NAP-2 | Monocytes Platelets | Platelet activators | | Neutrophils | Activates PMN |
| PF-4 | Platelets | Platelet activators | | Fibroblasts | ↑ Fibroblast growth Reverses immune suppression ↑ I-CAM1 on E.C. |
| IP-10/muCCRG-2 | Monocytes Fibroblasts Endothelial cells Keratinocytes | Endotoxin | IFN-γ | Monocytes Activated T lymphocytes | ↑ Chronic inflammation |
| ENA-78 | Epithelial cells | | IL-1 TNF | Neutrophils | Activates PMN |

This chemokine α group includes IL-8, melanoma growth-stimulating activity (MGSA/GRO), platelet factor 4 (PF-4), β thromboglobulin (βTG), IP-10, and ENA-78.

IL-8 is produced by many cell types including NK cells and T lymphocytes in response to exogenous stimuli such as polyclonal mitogens, injurious stimuli, and infectious agents, as well as proinflammatory cytokines such IL-1 and TNF. IL-8 is a chemoattractant of neutrophils, basophils, and a small proportion (10% or less) of resting $CD4^+$ and $CD8^+$ lymphocytes. IL-8 additionally activates neutrophil enzyme release. IL-8 is also haptotactic for melanocytes and is a comitogenic stimulant of keratinocytes.

IL-8 promotes the adherence of neutrophils to endothelial cells. IL-8 does so by inducing neutrophils to express $\beta_2$ integrins. Neutrophils then extravasate by moving between the endothelial cell junctions and through the basement membrane to accumulate in the tissues. Intracutaneous injections of IL-8 cause a rapid local neutrophilic infiltration peaking with 3 hours. Intravenous administration of IL-8 does not induce systemic sequelae of elevation of acute-phase proteins or fever but does induce a neutrophilia. Intravenous administration of IL-8 also specifically reduces local peripheral inflammatory responses to IL-8, fMLP, and C5a (Hechman et al. (1990) *FASEB J* 4:890). This transient anti-inflammatory effect of IL-8 probably can be attributed to desensitization of neutrophils by systemically distributed IL-8.

Two distinct but homologous (70% at the amino acid level) receptors for IL-8 have been cloned. The IL-8 receptors are members of the rhodopsin receptor family and have a seven transmembrane spanning region (Holmes et al. (1991) *Science* 253:1278; Murphy et al. (1991) *Science* 253:1280). The receptors are probably coupled to G-proteins, transduce phosphoinositol hydrolysis, and are capable of rapid elevation of diacylglycerol and cytosolic $Ca^{2+}$ levels, which may lead to activation of protein kinase C (Thelen et al. (1988) *FASEB J* 2:2702). IL-8 receptors are expressed by neutrophils, which display both types of IL-8R and their expression is unregulated by G-CSF (A. Lloyd et al., unpublished results). Mature neutrophils express about 20,000 receptors per cell. Myelocytic lines and basophils express several thousand receptors per cell.

IL-8 like molecules have been identified in rabbits, sheep, and other species. IL-8 is in the circulation of patients with systemic inflammatory reactions or severe trauma. IL-9 has readily been detected in inflammatory sites such as in the synovial fluid in rheumatoid arthritis (Brennan et al. (1990) *Eur J. Immunol* 20:2141), extracts of psoriatic skin (Schroder et al. (1986) *J Invest Dermatol* 87:53, and in the circulation of patients in septic shock (Van Zee et al. (1991) *J Immunol* 146:3478–3482). Thus IL-8 is implicated as a major participant in acute as well as more prolonged inflammatory reactions.

MGSA, as its name implies, was first discovered as a factor that accelerated the growth of melanoma cell lines and also as a product of oncogene transfected cell lines (GRO). MGSA/GRO competes for the type II, but not type I, IL-8 receptor on myelocytic cells (Lee (1992) *J Biol Chem* 267:16283–16287) and is also a potent chemoattractant, as well as activator of neutrophils. MGSA as well as IL-8 has been extracted from psoriatic tissues (Sticherling et al. (1991) *J Invest Dermatol* 96:26).

GRO has three variants (α, β, and γ), which exhibit about 95% homology in their amino acid sequences. They are probably homologues of murine macrophage derived KC, macrophage derived inflammatory peptides MIP-2α and MIP-2β. Murine MIP-2α and MIP-2β both compete with equal affinity for type II receptors for IL-8 and chemoattract human as well as murine neutrophils (Lee et al. (1992) *J. Biol Chem* 267:16283–16287). MIP-2 is also reported to degranulate murine neutrophils, resulting in the release of lysosomal enzymes. Local in vivo injections of MIP-2 results in neutrophil accumulation and MIP-2 has been isolated from sites of wound healing. MIL-2 is a costimulator of hematopoietic colony formation by CSF-1 and GM-CSF, but the in vivo relevance of this observation remains to be established. It is most likely that GRO/MIP-2 inflammatory activities overlap considerably with those of IL-8, and GRO is therefore probably also a major inflammatory mediator.

PF-4 and CTAP III, the precursor of βTG, are both present in platelet granules and are released by inducers of platelet aggregation. Consequently, they become available at sites of injury, hemorrhage, and thromboses. Both are reported to chemoattract and to stimulate fibroblasts, presumably for repair purposes. In addition, a 70 amino acid breakdown product of βTG known as neutrophil attracted peptide 2 (NAP-2) is a chemoattractant and activator of neutrophils, albeit at 100-fold higher concentrations that IL-8. NAP-2 also competes for the type II IL-8 receptor with about one-hundredth of the affinity of IL-8 (Leonard et al. (1991) *J. Leukoc Biol* 49:258). However, since at the site of platelet aggregation, high levels of NAP-2 can be released, it is thought to be an active participant in attracting inflammatory cells to such sites.

ENA-78 is the most recently cloned member of the chemokine α subfamily (Walz et al. (1991) *J Exp Med* 174:1355). ENA-78 is produced by an epithelial cell line in response to IL-1 and TNF. In cross-desensitization experiments, ENA-78 also utilizes the type II receptor for IL-8 and GRO and is a chemoattractant and activator of neutrophils.

IP-10 is produced by macrophages, endothelial cells, and keratinocytes in response to IFN-γ. The pathophysiological functions of IP-10 remain unclear, but antibodies to IP-10 react with many cell types present at sites of delayed hypersensitivity reactions and IP-10 has been extracted from psoriatic plaques (Gotlieb et al. (1988) *J Exp Med* 168:941). Thus IP-10 can presumably be produced by many cell types and probably participates in chronic inflammation and delayed hypersensitivity responses.

A stable recombinant human IP-10 was recently produced by Dr. K. Matsushima (personal communication). We have shown that this rhIP-10 is a moderately potent in vitro chemoattractant of human monocytes, but not neutrophils. In addition, this IP-10 also is a moderately potent chemoattractant for previously activated CD4 and CD8 T lymphocytes and promotes adhesion of lymphocytes to endothelial cells (D. Taub et al., unpublished results). These observations predict that IP-10 will probably be a participant in chronic cell-mediated inflammatory reactions.

There are two known human subtypes of the IL-8 receptor. Subtype A (CXCR1) binds IL-8 with high affinity ($K_d$=0.1 nM) but shows very low affinity binding to GROα and NAP-2 ($K_d$>100 nM). Subtype B (CXCR2) binds all three ligands with high affinity.

Overall, the chemokine family members appear to be very potent and pivotal chemoattractants and activators of inflammatory cells and fibroblasts. The aforementioned inflammatory cytokines have myriad effects on cell growth and differentiation. Some of these effects are indirect and based on the capacity of cytokines to induce the production of a cascade of other cytokines. Therapeutic usefulness of cytokines and their inhibitors is growing and should accelerate.

In recent years drug discovery has been advanced by expression of heterologous receptors in living cells. However, due to the complexities inherent in such heterologous expression studies, the development of reliable assays to search for modulators of these receptors has presented particular challenges. For example, it is often difficult to obtain sufficient expression of heterologous G protein-coupled receptors or to achieve functional integration of the G protein-coupled receptor into a signaling pathway. Price et al. have reported the functional coupling of a rat A2a adenosine receptor into the yeast pheromone response pathway (Price et al. (1996) *Molec. Pharmacol.* 50:829–837), but only achieved effective coupling when they coexpressed the native yeast G protein GPA1, expressed from a plasmid, in the yeast cells. They were unable to achieve effective coupling using either a mammalian Gα subunit protein or a chimeric Gα subunit protein expressed in the yeast cells. The development of expression and coupling systems for expression of modified G protein coupled receptors which display altered ligand binding and/or coupling in host cells would be of tremendous benefit in the development of improved drug screening assays for modulators of G protein coupled receptors.

SUMMARY OF THE INVENTION

The present invention is based, in part, upon studies investigating the coupling of the IL8A receptor to the pheromone response pathway in yeast through a Gpa1–Gαi2 chimera. By random mutagenesis of this receptor, mutants have been identified that show altered coupling behavior to the ligands GROα and NAP-2 as well as showing an enhanced response to IL8. Based upon these studies, an amino acid motif has been identified in the IL8 receptor. Mutations made in this region can affect ligand binding and/or coupling of the receptor to the signal transduction machinery of the cell. Other receptors also have this motif and corresponding mutations can be made in such receptors, e.g., the galanin receptor-1 to enhance signaling by those receptors through Gpa1–Gαi2.

Thus, the present invention provides host cells that express modified G protein coupled receptors which are functionally integrated into the pheromone response pathway of the cells such that the cells display ligand dependent responses to the modified receptor which differ from responses seen upon modulation of the wild type receptor. The cells of the invention can be used to identify modulators (e.g., agonists or antagonists) of such receptors. In particular, the invention provides cells expressing modified mammalian IL-8 or galanin receptors (e.g., IL8A or galanin-1 receptors). When yeast cells are used as the host cells, yeast cells may achieve functional coupling of the heterologous G protein coupled receptor using a mammalian G protein subunit protein or a chimeric G protein subunit expressed in the yeast cells. The invention also provides for mammalian cells which express these modified forms of G protein-coupled receptors.

In one embodiment, the invention provides a mutant mammalian G-protein coupled receptor having a sequence which varies from a wild type G protein-coupled receptor having a wild type amino acid sequence comprising an amino acid motif [$X_1X_2X_3X_4$] lying near the carboxy terminal end of said domain, wherein:

$X_1$ denotes an amino acid residue at position 1 of said motif and is selected from the group consisting of Phe, Leu, Val, and Tyr;

$X_2$ denotes an amino acid residue at position 2 of said motif and is selected from the group consisting of Phe, Lys and Gln;

$X_3$ denotes an amino acid residue at position 3 of said motif and is selected from the group consisting of Leu, Arg, Glu, Asn, Gln, Ser, Ala, Leu; and $X_4$ denotes an amino acid residue at position 4 of said motif and is selected from the group consisting of Ala, Cys, Asp, Glu, Gly, Ser, Thr and Tyr; and wherein said mutant receptor comprises a seventh transmembrane domain with a carboxy terminal end;

at least one point mutation at a position in said amino acid motif;

such that upon interaction with a ligand to modulate a signal transduction pathway in a cell, a signal generated by said mutant receptor is greater than a signal generated upon interaction of said ligand with a wild type G protein-coupled receptor.

In one embodiment, the host cell is a yeast cell. In a preferred embodiment, the receptor acts as a surrogate for an endogenous yeast pheromone receptor in a pheromone response pathway of said cell. In a particularly preferred embodiment, the cell belongs to the species *Saccharomyces cerevisiae*.

In one embodiment, the cell is a mammalian cell.

In one embodiment, interaction of ligand with a wild type G protein-coupled receptor generates no detectable signal. In one embodiment, the mutant receptor comprises an Arg or Lys at position 4.

In one embodiment, the heterologous receptor is an IL8A receptor.

In a preferred embodiment the point mutation in the receptor is selected from the group consisting of: Arg to Trp at position 73, Met to Ile at position 246; and Gly to Arg at position 320.

In one embodiment, the ligand of the receptor is interleukin 8 (IL8) or melanoma growth-stimulating activity-alpha (MGSA/GROα).

In a preferred embodiment, the receptor is a human receptor.

In another preferred embodiment the receptor is selected from the group consisting of human galanin-1 receptor, somatostatin receptor type I, somatostatin receptor type II, somatostatin receptor type III, and human nociceptin receptor. In particularly preferred embodiments, the receptor is a human galanin-1 receptor.

In preferred embodiments, the receptor comprises an amino acid sequence LAYSNSSVNPIIYAFLSEN[FRKR]YKQV (SEQ ID NO: 1) wherein said mutant amino acid motif within said sequence is [FRKR] (SEQ ID NO: 2).

In another aspect, the invention provides a recombinant yeast cell having a mutant form of a mammalian G protein-coupled receptor expressed in a membrane of said yeast cell, said mutant receptor having a sequence that varies from a wild type G protein-coupled receptor having a wild type amino acid sequence comprising an amino acid motif $[X_1X_2X_3X_4]$ lying near the carboxy terminal end of said domain, wherein:

$X_1$ denotes an amino acid residue at position 1 of said motif and is selected from the group consisting of Phe, Leu, Val, and Tyr;

$X_2$ denotes an amino acid residue at position 2 of said motif and is selected from the group consisting of Phe, Lys and Gln;

$X_3$ denotes an amino acid residue at position 3 of said motif and is selected from the group consisting of Leu, Arg, Glu, Asn, Gln, Ser, Ala, Leu; and $X_4$ denotes an amino acid residue at position 4 of said motif and is selected from the group consisting of Ala, Cys, Asp, Glu, Gly, Ser, Thr and Tyr; and wherein said mutant receptor comprises:

a seventh transmembrane domain with a carboxy terminal end; and at least one point mutation at a position on said amino acid motif;

wherein said mutant receptor acts as a surrogate for an endogenous yeast pheromone receptor in a pheromone response pathway of the yeast cell, such that upon interaction with a ligand to modulate signal transduction in said pheromone response pathway, a signal generated by said mutant receptor is greater than a signal generated upon interaction of said ligand with a wild type G protein-coupled receptor.

In a preferred embodiment, the yeast cell comprises a human receptor.

In another preferred embodiment, the yeast cell expresses a heterologous receptor selected from the group consisting of human galanin-1 receptor, somatostatin receptor type I, somatostatin receptor type II, somatostatin receptor type III, and human nociceptin receptor. In another preferred embodiment, the yeast cell expresses an IL8A receptor.

In another preferred embodiment, the yeast cell expresses a mammalian, chimeric, and/or mutant G protein subunit. In another preferred embodiment, the yeast cell expresses a mammalian, chimeric, and/or mutant Gα subunit. In a preferred embodiment, the yeast cell expresses a GPA41-$G_{\alpha i2}$ subunit. In another embodiment, the yeast cell expresses a GPA41-$G_{\alpha i1}$ or GPA41-$G_{\alpha i3}$ subunit.

In another embodiment, the yeast cell expresses a STE18-Gγ2 subunit.

In another embodiment, the yeast cell expresses a mammalian $G_{\alpha s}$E10K subunit.

In another embodiment, the yeast cell expresses a mammalian $G_{\alpha s}$D229S subunit or a mammalian $G_{\alpha s}$E10K+D229S subunit.

In one embodiment, the yeast cell is a mutant cell having a pheromone response pathway that is desensitized at slower rate than a wild type strain under the same conditions of continuous stimulation of the pheromone response pathway. In one embodiment, the yeast cell has a ste14 mutation.

In another embodiment, the yeast cell of claim 15, which has a ste2 or ste3 mutation. In another embodiment, the endogenous pheromone gene is not functionally expressed in the yeast cell. In yet another embodiment, an endogenous FAR1 gene is not functionally expressed in the yeast cell. In a further embodiment, an endogenous SST2 gene is not functionally expressed in the yeast cell.

In another embodiment, the yeast cell comprises a detectable or selectable marker that is activated by a pheromone response pathway of the yeast cell.

In one embodiment, the selectable marker comprises a pheromone-responsive promoter operably linked to a selectable gene.

In one embodiment, the pheromone-responsive promoter is the FUS1 promoter.

In another embodiment, the marker gene is a HIS 3 gene or a LacZ gene.

In another embodiment, the yeast cell further comprises a heterologous polypeptide, wherein the heterologous polypeptide is transported to a location allowing interaction with the region of said receptor expressed in the cell membrane and wherein modulation of the signal transduction of said receptor by the heterologous polypeptide provides a detectable signal.

In one embodiment, the heterologous polypeptide includes a signal sequence. In another embodiment, the signal sequence corresponds to a leader peptide of the *Saccharomyces cerevisiae* α factor or a-factor.

In preferred embodiments, the yeast cells are *Saccharomyces cerevisiae* cells.

In another aspect, the invention pertains to a method for identifying a modulator of a mammalian G-coupled protein receptor expressed by a yeast cell, comprising:

(i) contacting a mixture of yeast cells with a test compound;

(ii) allowing cells within the mixture to generate a detectable signal; and (iii) identifying the test compound as a modulator of said receptor expressed by the yeast cell.

DESCRIPTION OF THE DRAWINGS

FIG. 9 shows pertussis toxin sensitivity of the ligand induced $Ca^{2+}$ flux in mammalian HEK293/Gα16 cells expressing wild type or mutant IL8 receptors

DETAILED DESCRIPTION OF THE INVENTION

Figure 1:
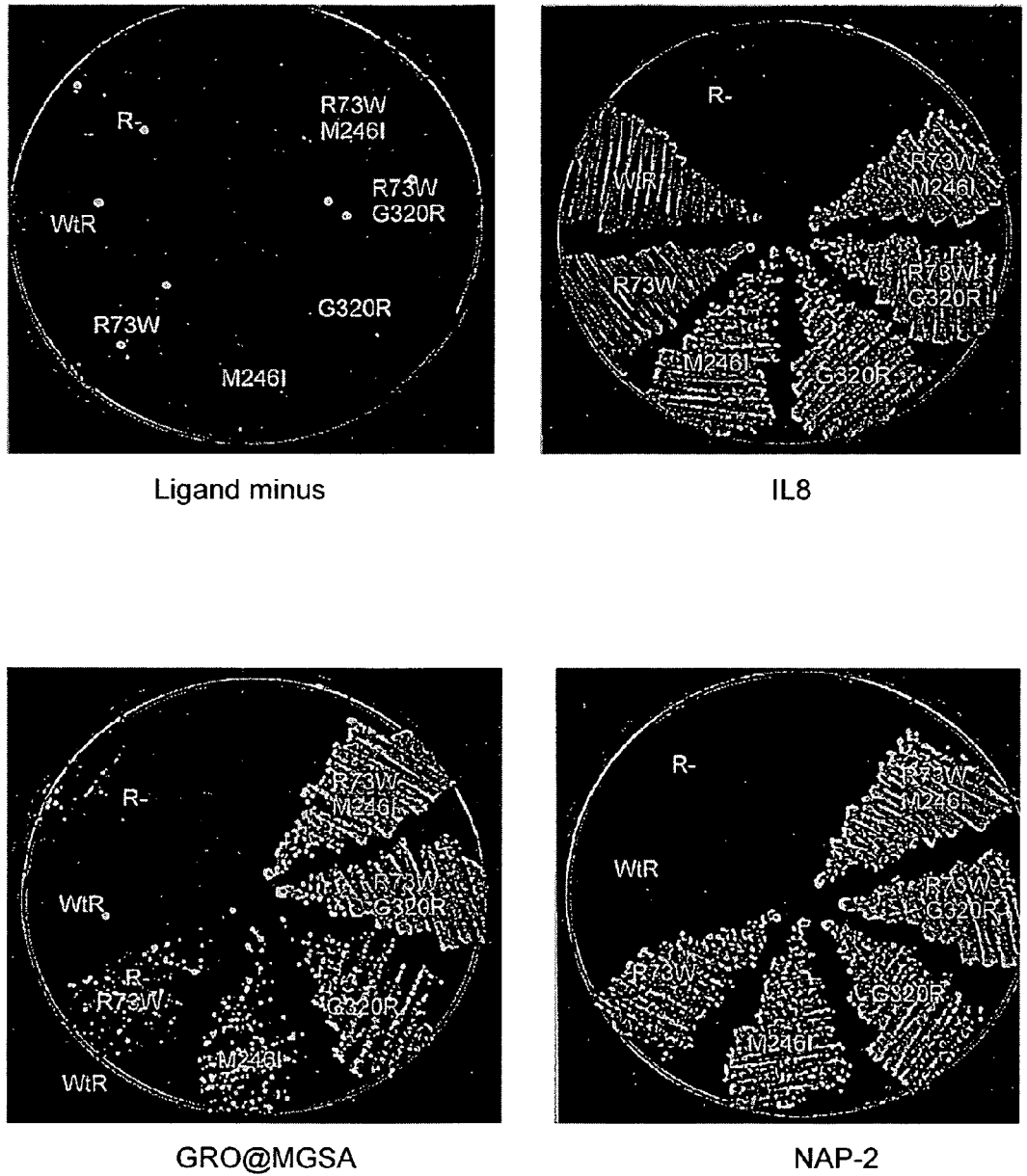
FIG. 1 shows ligand induced growth of cells expressing wild type or mutant IL8 receptors and the indicated ligand.

The present invention provides modified forms of G protein coupled receptors which display altered ligand binding and/or coupling properties. The invention also provides cells expressing such receptors and assays utilizing these cells for screening and identifying pharmaceutically effective compounds that specifically modulate the activity of a these modified forms of G protein coupled receptors. Yeast or mammalian cells can be used to express such receptors. The subject assays enable rapid screening of large numbers of compounds (e.g., compounds in a library) to identify those which are receptor agonists or antagonists. Compositions of matter, such as these novel receptors, novel recombinant yeast cells and novel gene constructs, are also embraced by the present invention. The instant assays provide a convenient format for discovering compounds which can be useful in modulating cellular function, as well as in understanding the pharmacology of compounds that specifically interact with these modified forms G protein coupled receptors.

In the practice of the instant invention, standard techniques known in the art can be used. See for example, Sherman. 1991. Methods Enzymol. 194:3; Sherman and Hicks. 1991. Methods Enzymol. 194:21; Sambrook et al. *Molecular Cloning A Laboratory Manual*, 2nd Ed., ed. by Sambrook, Fritsch and Maniatis (Cold Spring Harbor Laboratory Press: 1989 or 1991 edition.

Before further description of the invention, certain terms employed in the specification, examples and appended claims are, for convenience, collected here.

I. Definitions

The term "compound" as used herein (e.g., as in "test compound") is meant to include both exogenously added test compounds and peptides endogenously expressed by a cell, e.g., from a peptide library. For example, in certain embodiments, the reagent cell also produces the test compound which is being screened. For instance, the reagent cell can produce. e.g., a test polypeptide, a test nucleic acid and/or a test carbohydrate which is screened for its ability to modulate the heterologous receptor activity. In such embodiments, a culture of such reagent cells will collectively provide a library of potential effector molecules and those members of the library which either agonize or antagonize the receptor function can be selected and identified. Moreover, it will be apparent that the reagent cell can be used to detect agents which transduce a signal via the receptor of interest.

In one embodiment, the compound is a ligand for the receptor, e.g., a compound which interacts with the receptor, whether naturally occurring or nonnaturally occurring. As used herein, the language "interacts with" includes receptor-ligand interactions, e.g., binding interactions. Preferably, when a ligand "interacts with" a receptor, the receptor transduces a signal in the cell expressing the receptor, such that a signal transduction pathway is modulated, e.g., affected in the cell.

In other embodiments, the test compound is exogenously added. In such embodiments the test compound is contacted with the reagent cell. Exemplary compounds which can be screened for activity include, but are not limited to, peptides, nucleic acids, carbohydrates, small organic molecules, and natural product extract libraries. In such embodiments, both compounds which agonize or antagonize the receptor mediated signaling function can be selected and identified.

The term "non-peptidic compound" is intended to encompass compounds that are comprised, at least in part, of molecular structures different from naturally-occurring L-amino acid residues linked by natural peptide bonds. However, "non-peptidic compounds" are intended to include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds. "Non-peptidic compounds" also are intended to include natural products.

As used herein, "recombinant cells" include any cells that have been modified by the introduction of heterologous DNA. Exemplary control cells include cells that are substantially identical to the recombinant cells, but do not express one or more of the proteins encoded by the heterologous DNA, e.g., do not include or express a reporter gene construct, receptor or test polypeptide, or express a different heterologous DNA (e.g., a cell that expresses a different GPCR that couples to the same G protein as that of the GPCR whose activity is being examined).

As used herein, "heterologous DNA" or "heterologous nucleic acid" includes DNA that does not occur naturally as part of the genome in which it is present or which is found in a location or locations in the genome that differs from that in which it occurs in nature or which is operatively linked to DNA to which it is not normally linked in nature (i.e., a gene that has been operatively linked to a heterologous promoter). Heterologous DNA is not naturally occurring in that position or is not endogenous to the cell into which it is introduced, but has been obtained from another cell. Heterologous DNA can be from the same species or from a different species. In some embodiments, it is mammalian, e.g., human. Any DNA that one of skill in the art would recognize or consider as heterologous or foreign to the cell in which is expressed is herein encompassed by the term heterologous DNA. Examples of heterologous DNA include, but are not limited to, genes which encode proteins that amplify signals transduced via the pheromone response pathway, DNA that encodes test polypeptides, receptors, reporter genes, transcriptional and translational regulatory sequences, or selectable or traceable marker proteins, such as a protein that confers drug resistance.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, the term "high copy number plasmid" refers to a plasmid which exists in at least 5, or more, copies per cell, and more preferably in at least 10–20 copies per cell. The term "low copy number plasmid" refers to a plasmid which exists in fewer than 5 copies per cell, more preferably 2–3 copies, or less, per cell.

As used herein, the term "extracellular signal" is intended to encompass molecules and changes in the environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface receptors and modulate the activity of such receptors. The term, "extracellular signal" also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

As used herein, "heterologous G protein receptor" (e.g., a heterologous adenosine receptor) is encoded by heterologous DNA and, upon expression of this heterologous DNA in a recombinant cell, the heterologous receptor is expressed in the recombinant cell.

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation.

A "signaling pathway" refers to the components involved in "signal transduction" of a particular signal into a cell. The term "endogenous signaling pathway" indicates that some or all of the components of the signaling pathway are naturally-occurring components of the cell. An example of such a pathway is the endogenous pheromone response pathway of yeast.

The term "functionally couples to" (as in a receptor that is "functionally integrated into a signaling pathway in a cell" or "functionally integrated into an endogenous yeast signaling pathway" or "functionally expressed by a host cell") is intended to refer to the ability of the receptor to be expressed at the surface of the cell and the ability of the expressed receptor to bind to modulators (e.g., a ligand of the receptor) and transduce signals into the cell via components of a signaling pathway of the cell. For example, a G protein-coupled receptor (GPCR) which is functionally integrated into an endogenous pheromone response or signaling pathway of a yeast cell is expressed on the surface of the yeast cell, couples to a G protein within the yeast cell and transduces a signal in that yeast cell upon binding of a modulator to the receptor. For example, a G protein subunit, e.g., a chimeric, mutant or heterologous subunit, that is functionally integrated into a yeast cell may be capable of coupling both to the GPCR and to the other G protein subunits, which can also be endogenous to the yeast cell, can be chimeric, or can be heterologous. Alternatively, the G protein subunit can be constitutively active such that it need not be coupled to a heterologous GPCR. A transduced signal may be detected by measuring any one of a number of responses to mating factors which occur in a yeast cell, e.g., growth arrest or transcription of an indicator gene responsive to signals produced by modulation of a pheromone response pathway or any biochemical changes.

The term "indicator gene" generically refers to an expressible (e.g., able to transcribed and (optionally) translated) DNA sequence which is expressed in response to a signal transduction pathway modulated by a target receptor or ion channel. Exemplary indicator genes include unmodified endogenous genes of the host cell, modified endogenous genes, or a reporter gene of a heterologous construct, e.g., as part of a reporter gene construct.

The term "endogenous gene" is intended to refer to a gene in a cell that is naturally part of the genome of the cell and which, most preferably, is present in its natural location in the genome (as opposed to "heterologous" DNA which has been introduced into the cell). Likewise, the term "endogenous protein" is intended to include proteins of a cell that are encoded by endogenous genes of the cell.

An endogenous gene that is to be used as an indicator gene may comprise the natural regulatory elements of the gene (e.g., the native promoter/enhancer elements that naturally regulate expression of the gene) or the endogenous gene can be "operatively linked to" (i.e., functionally coupled to) a "heterologous promoter" (or other heterologous regulatory elements). A "heterologous promoter" refers to a promoter that does not naturally regulate the gene to which the heterologous promoter is operatively linked. For example, an endogenous yeast gene that is not normally pheromone-responsive can be operatively linked to a heterologous promoter that is responsive to signals produced by the yeast pheromone system to thereby confer pheromone responsiveness on the endogenous yeast gene. Methods of using endogenous yeast genes as indicator genes are described further in PCT Publication WO 98/13513, the contents of which are hereby expressly incorporated herein by this reference.

The term "detecting an alteration in a signal produced by an endogenous signaling pathway" (e.g., an endogenous yeast signaling pathway) is intended to encompass the detection of alterations in endogenous second messengers produced upon activation of components of the endogenous signaling pathway, alterations in endogenous gene transcription induced upon activation of components of the endogenous signaling pathway, and/or alterations in the activity of an endogenous protein(s) upon activation of components of the endogenous signaling pathway. In certain embodiments, the term "detecting an alteration in a signal produced by an endogenous signaling pathway" can also encompass assaying general, global changes to the cell such as changes in cell growth or cell morphology.

As used herein, a "reporter gene construct" refers to a nucleic acid that includes a "reporter gene" operatively linked to a transcriptional regulatory sequences. Transcription of the reporter gene is controlled by these sequences. The activity of at least one or more of these control sequences is directly or indirectly regulated by the target receptor protein. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences which are recognized by effector molecules, including those that are specifically induced by interaction of an extracellular signal with the target receptor. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional regulatory elements or sequences. In addition, the construct may include sequences of nucleotides that alter translation of the resulting mRNA, thereby altering the amount of reporter gene product. The reporter gene constructs of the present invention provide a detectable readout in response to signals transduced in response to modulation of a heterologously expressed receptor.

The term "modulation", as in "modulation of a (heterologous) G protein coupled receptor" and "modulation of a signal transduction activity of a receptor protein" is intended to encompass, in its various grammatical forms, induction and/or potentiation, as well as inhibition and/or downregulation of receptor activity and/or one or more signal transduction pathways downstream of a receptor.

Agonists and antagonists are "receptor effector" molecules that modulate signal transduction via a receptor. Receptor effector molecules are capable of binding to the receptor, though not necessarily at the binding site of the natural ligand or otherwise modulating the activity of the receptor, for example, by influencing the activity of components which regulate the receptor, or which function in the signal transduction initiated by the receptor. Receptor effectors can modulate signal transduction when used alone, i.e. can be surrogate ligands, or can alter signal transduction in the presence of the natural ligand or other known activators, either to enhance or inhibit signaling by the natural ligand. For example, "antagonists" are molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor.

The term "surrogate ligand" refers to an agonist which induces signal transduction from a receptor; the agonist is a surrogate in that it is not the natural ligand of the receptor.

The term "autocrine cell", as used herein, refers to a cell which produces a substance which can stimulate a receptor located on or within the same cell as that which produces the substance. For example, wild-type yeast MATα and MATa cells are not autocrine. However, a yeast cell which produces both α-factor and α-factor receptor, or both a-factor and a-factor receptor, in functional form, is autocrine. By extension, cells which produce a peptide which is being screened for the ability to activate a receptor (e.g., by activating a G protein-coupled receptor) and also express the receptor are called "autocrine cells". In some instances, such cells can also be referred to as "putative autocrine cells" since some of the cells will express peptides from the library which will not activate the receptor which is expressed. In a library of such cells, in which a multitude of different peptides are produced, it is likely that one or more of the cells will be "autocrine" in the stricter sense of the term.

As used herein, the term "not produced in functional form" with regard to endogenous yeast proteins is intended to encompass proteins which are not produced in functional form for any number of reasons, for example, because of a mutation to the gene which encodes the protein or a deletion, e.g., a disruption, of the gene which encodes the protein. The term "not produced in functional form" is also intended to include conditional mutations (e.g. temperature sensitive mutation), wherein the protein is not produced in functional form under certain conditions. The term also includes proteins (e.g., in a mutant yeast cell) that are not folded correctly (i.e., the tertiary structure doesn't resemble that of the protein when normally expressed in functional form).

As used herein the term amino acid "motif" refers to an amino acid sequence of a wild type G protein-coupled receptor which can be mutated to give the receptor altered ligand binding and/or coupling properties. The amino acid sequence motif of a G protein coupled receptor can be represented by the amino acid sequence $[X_1X_2X_3X_4]$ (where $X_1$ is Phe, Leu, Val, or Tyr; $X_2$ is Phe, Lys, or Gln; $X_3$ is Leu, Arg, Glu, Asn, Gln, Ser, Ala, or Leu; and $X_4$ is Ala, Cys, Asp, Glu, Gly, Ser, Thr, or Tyr). Preferably the amino acid motif lies near the carboxy terminal end of a G protein coupled receptor, e.g., near the carboxy terminal end of the seventh transmembrane domain.

II. General Overview of Assay

As set out above, the present invention relates to yeast cell compositions and methods for identifying effectors of modified G protein coupled receptor protein or receptor protein complexes. The instant assays are characterized by the use of a mixture of recombinant cells to sample test compounds for receptor agonists or antagonists. As described in greater detail below, the reagent cells express a heterologous modified form of a G protein coupled receptor functionally integrated into the cell and capable of transducing a detectable signal in the yeast cell. Compounds which either agonize or antagonize the receptor function can be selected and then identified based on biochemical signals produced by the receptor, or any more distal result of receptor-mediated stimulation, for example increases in endogenous mRNA expression, etc., or, in some embodiments, by the use of reporter genes responsive to such signals. In certain embodiments, the library of compounds to be tested is a library of peptides which is expressed by the yeast cells and causes stimulation in an autocrine fashion.

The ability of compounds to modulate the signal transduction activity of the target receptor can be scored for by detecting up or down-regulation of the detection signal. For example, GTPase activity, phospholipid hydrolysis, or protein phosphorylation stimulated by the receptor can be measured directly. Alternatively, the use of a reporter gene can provide a readout. In any event, a statistically significant change in the detection signal can be used to facilitate isolation of compounds of interest.

In certain embodiments, the cells for use in the instant assays express a modified form of a heterologous G protein-coupled receptor, e.g., an IL8 or a galanin receptor, and an endogenous G protein subunit which couples to that receptor. In one embodiment, the cells are yeast cells. Preferably, the G protein coupled receptors of the present invention have been modified such that coupling of the receptor to an endogenous cell signaling pathway, e.g, the pheromone system pathway of a yeast cell, is enhanced. For example, in preferred embodiments, the yeast cells express a heterologous G protein coupled receptor which is mutated such that it displays altered ligand binding and coupling properties from the wild type receptor, thus facilitating enhanced response of that receptor to a particular ligand or enhanced coupling of the receptor in response to a ligand when expressed in the host cell. In a preferred embodiment, the host cells express a modified form of a heterologous IL-8 receptor or a modified form of a heterologous galanin receptor and a heterologous or chimeric G protein subunit. In particularly preferred embodiments, e.g., when the host cell is a yeast cell, the heterologous G protein receptor and the heterologous G protein subunit are of the same origin, e.g., mammalian. In yet another preferred embodiment, the host cells express a mutated heterologous G protein subunit.

In still another preferred embodiment, the host cells, e.g., yeast cells express a chimeric G protein subunit. In particularly preferred embodiments the heterologous G protein coupled receptor and the heterologous segment of the chimeric G protein subunit are derived from the same source. For example, for a mammalian G protein coupled receptor, the chimeric G protein subunit preferably comprises a portion of a yeast G protein and a portion of a mammalian G protein subunit (e.g., human or rat). In more preferred embodiments, the second amino acid sequence in the G protein subunit chimera is derived from a mammalian G protein subunit. In particularly preferred embodiments, the second amino acid sequence is derived from a human G protein subunit sequence.

It will further be understood that the above embodiments are not mutually exclusive. For example, in certain preferred embodiments, a yeast cell expressing a heterologous G protein coupled receptor may express a first mutated or chimeric G protein subunit and a second, different mutated or chimeric G protein subunit to enhance coupling to the heterologous receptor.

In certain embodiments the yeast cells also express an indicator gene that produces a detectable signal upon functional coupling of the heterologous G protein coupled receptor to the G protein. In certain embodiments the indicator gene is a reporter gene construct which including a reporter gene in operative linkage with one or more transcriptional regulatory elements responsive to the signal transduction activity of the target receptor, with the level of expression of the reporter gene providing the receptor-dependent detection signal. The amount of transcription from the reporter gene may be measured using any method known to those of skill in the art. For example, specific mRNA expression may be detected using Northern blots or specific protein product may be identified by a characteristic stain or an intrinsic activity. In preferred embodiments, the gene product of the reporter is detected by an intrinsic activity associated with that product. For instance, the reporter gene may encode a gene product that, by enzymatic activity, gives rise to a detection signal based on color, fluorescence, or luminescence.

The amount of activation of the indicator gene, e.g., expression of a reporter gene, is then compared to the amount of expression in either the same cell in the absence of the test compound or it may be compared with the amount of transcription in a substantially identical cell that lacks the specific receptors or that expresses a different receptor (e.g., a different GPCR that couples to the same G protein subunit as the test receptor). A control cell may be derived from the same cells from which the recombinant cell was prepared but which had not been modified by introduction of heterologous DNA, e.g., the DNA encoding a test polypeptide. Alternatively, it may be a cell in which the specific receptors are removed. Any difference, e.g., a statistically significant difference, in the amount of transcription indicates that the test compound has in some manner altered the activity of the specific receptor.

In other preferred embodiments, the reporter gene provides a selection method such that cells in which the compound is an effector for the receptor have a growth advantage. For example the reporter could enhance cell viability, relieve the nutritional requirement of a cell, and/or provide resistance to a drug.

By using any one of these readouts, compounds which modulate signaling via the heterologous receptor can be selected. If the compound does not appear to modulate signaling via the receptor protein, the assay may be repeated and modified by the introduction of a step in which the recombinant cell is first contacted with a known activator of the target receptor to induce signal transduction from the receptor, and the compound is assayed for its ability to inhibit the activity of the receptor, e.g., to identify receptor antagonists. In yet other embodiments, compounds can be screened for members which potentiate the response to a known activator of the receptor.

III. Heterologous G Protein Coupled Receptors

Any wild type G protein-coupled receptor comprising an amino acid motif [$X_1X_2X_3X_4$] (where $X_1$ is Phe, Leu, Val, or Tyr; $X_2$ is Phe, Lys, or Gln; $X_3$ is Leu, Arg, Glu, Asn, Gln, Ser, Ala, or Leu; and $X_4$ is Ala, Cys, Asp, Glu, Gly, Ser, Thr, or Tyr) lying near the carboxy terminal end of the receptor, e.g., near the carboxy terminal end of the seventh transmembrane domain, can be modified according to the invention to display altered ligand binding and/or coupling properties. For example, the IL8A receptor has been found to comprise the amino acid sequence LGFLHSCLNPI-IYAFIGQN[FRNG]FLKM (SEQ ID NO: 3). The amino acid motif is seen in the [FRNG] (SEQ ID NO:4) sequence. A mutation in the Gly residue (amino acid 320 of the receptor) of this motif (to an Arg residue) has been found to result in altered ligand binding and/or coupling properties.

Other G protein coupled receptor amino acid sequences can be scanned for this same motif or can be aligned with the IL8a receptor motif. The galanin receptor has also been found to have this motif. An alignment of the IL8 and galanin receptor motifs are presented below.

LGFLHSCLNPIIYAFIGQN[FRN<u>G</u>]FLKM rIL8aR (SEQ ID NO: 3)

LAYSNSSVNPIIYAFLSEN[FRK<u>A</u>]YKQV hGalR1 (SEQ ID NO: 5)

Corresponding mutations can be made in the amino acid motif in other receptors to impart similar properties onto those receptors. Exemplary G protein coupled receptors having this motif are described below.

IL8 Receptors

IL-8 is produced by many cell types including NK cells and T lymphocytes in response to exogenous stimuli such as polyclonal mitogens, injurious stimuli, and infectious agents, as well as proinflammatory cytokines such IL-1 and TNF. IL-8 is a chemoattractant of neutrophils, basophils, and a small proportion (10% or less) of resting $CD4^+$ and $CD8^+$ lymphocytes. IL-8 is an important mediator of inflammation. It activates neutrophil enzyme release and is also haptotactic for melanocytes and is a comitogenic stimulant of keratinocytes.

In one embodiment, the host cells of the invention express a heterologous, preferably a modified form, of an IL8 receptor functionally integrated into a signaling pathway of the host cell. In one embodiment, the host cell is a yeast cell. In another embodiment, the host cell is a mammalian cell. In preferred embodiments, the IL-8 receptor is a mammalian receptor. In one aspect, the invention pertains to a recombinant yeast cell comprising a modified, heterologous (e.g., human) IL8 receptor expressed in a membrane of the yeast cell such that signal transduction activity via the heterologous (e.g., human) IL8 receptor is modulated by interaction of a region of the heterologous (e.g., human) IL8 receptor with an extracellular signal and such that signal transduction is altered from that seen in wild type receptors. In one embodiment, the host cell is a yeast cell and the heterologous (e.g., human) IL8 receptor acts as a surrogate for an endogenous yeast pheromone receptor in a pheromone response pathway of the yeast cell. Modulation of the signal transduction activity of the heterologous (e.g., human) IL8 receptor by an extracellular signal in the host cell provides a detectable signal.

In one embodiment, a human G protein coupled receptor expressed by the host cells is an IL-8 receptor. In a preferred embodiment, the cell is an IL8A receptor.

Galanin Receptors.

Galanin is a neuroendocrine peptide which is approximately 29 amino acids in length and is grcognized by G protein coupled central nervous system receptors via its N-terminus.

In one embodiment, the host cells of the invention express a heterologous, and preferably a modified form of an galinin receptor, functionally integrated into a signaling pathway of the host cell. In one embodiment, the host cell is a yeast cell. In another embodiment, the host cell is a mammalian cell. In preferred embodiments, the galinin receptor is a mammalian receptor. In one aspect, the invention pertains to a recombinant yeast cell comprising a modified, heterologous (e.g., human) galinin receptor expressed in a membrane of the yeast cell such that signal transduction activity via the heterologous (e.g., human) galinin receptor is modulated by interaction of a region of the heterologous (e.g., human) galinin receptor with an extracellular signal and such that signal transduction is altered from that seen in wild type receptors. In one embodiment, the host cell is a yeast cell and the heterologous (e.g., human) galinin receptor acts as a surrogate for an endogenous yeast pheromone receptor in a pheromone response pathway of the yeast cell. Modulation of the signal transduction activity of the heterologous (e.g., human) galinin receptor by an extracellular signal in the host cell provides a detectable signal.

In one embodiment, a human G protein coupled receptor expressed by the host cells is an galinin receptor.

To facilitate expression of a heterologous (e.g., human) G protein receptor in a host cell, e.g., a yeast cell, the coding sequence for the receptor can be operatively linked to a heterologous (e.g., yeast) leader sequence. Examples of heterologous leader sequences that can be used include the leader sequence of the yeast Ste2 receptor and the invertase leader sequence. Moreover, the leader sequence of yeast α-factor is often used to express heterologous receptors in yeast cells. Use of heterologous leader sequences to promote the expression of the G protein coupled receptor in yeast cells is discussed in further detail in subsections below.

In preferred embodiments, the yeast cell expresses a mammalian, chimeric, and/or mutant G protein subunit, in addition to the heterologous (e.g., human) G protein coupled receptor. This mammalian, chimeric, and/or mutant G protein subunit can be, for example, a mammalian, chimeric, and/or mutant Gα subunit. Alternatively or additionally, the yeast cell can express a mammalian, chimeric, and/or mutant Gγ subunit. The structure and use of these mammalian and chimeric G protein subunits are described in further detail in subsections below.

When the yeast cell expresses an heterologous G protein coupled receptor (e-g., a modified G protein coupled receptor), the yeast cell preferably also expresses a chimeric G protein, e.g., a Gα subunit that is a GPA41-$G_{\alpha i2}$ subunit. Other preferred chimeric Gα subunits for use with heterologous G protein coupled receptors include a GPA41-$G_{\alpha i1}$ and GPA41-$G_{\alpha i3}$ subunit. In one embodiment, the yeast cell expresses a chimeric STE18-Gγ subunit. In one embodiment, the yeast cell expresses both a chimeric Gα subunit and a chimeric STE18-Gγ subunit.

In one embodiment, the yeast cell preferably also expresses a mutant G protein subunit e.g., a mammalian $G_{\alpha s}$ having a E10K (i.e., Glu to Lys substitution at position 10) mutation. Other preferred chimeric Gα subunits for use with heterologous G protein coupled receptor include a mammalian $G_{\alpha s}$D229S subunit or a mammalian $G_{\alpha s}$E10K+D229S subunit. In other embodiments the yeast cell expresses endogenous GPA1.

In preferred embodiments, a yeast cell of the invention that expresses an G protein coupled receptor is a mutant cell having a pheromone response pathway that is desensitized at a slower rate than a wild type strain under the same conditions of continuous stimulation of the pheromone response pathway. In one embodiment, an endogenous FAR1 gene is not functionally expressed in the yeast cell. In another embodiment, an endogenous SST2 gene is not functionally expressed in the yeast cell. In still other embodiments, the yeast cell has a ste14 mutation or has a ste2 or ste3 mutation. In yet other embodiments, an endogenous pheromone gene is not functionally expressed in the yeast cell. Various preferred mutations that can be present in the yeast cells used as host cells for expression of a heterologous receptor are described in further detail in subsections below.

To facilitate detection of signaling through the heterologous G protein coupled receptor expressed by a yeast cell of the invention, the yeast cell preferably further comprises a selectable marker that is activated by a pheromone response pathway of the yeast cell, thereby providing the detectable signal. The marker gene can be can comprise, for example, a pheromone-responsive promoter operably linked to a selectable gene or a detectable gene. An example of a suitable pheromone-responsive promoter is the FUS1 promoter. An example of suitable marker genes are the HIS 3 gene and the LacZ gene. Generation of detectable signals, and use of markers for detection thereof, are described in further detail in subsections below.

In another embodiment of the invention, in addition to expression of a heterologous G protein coupled receptor the yeast cells also express a heterologous polypeptide. The heterologous polypeptide is transported to a location allowing interaction with a region of the heterologous (e.g., human) receptor expressed in the cell membrane of the yeast cell. Such peptides may act at sites other than extracellular binding sites. Modulation of the signal transduction activity of the heterologous (e.g., human) receptor by the heterologous polypeptide provides a detectable signal. Thus, in this embodiment, the heterologous polypeptide and the heterologous G protein coupled receptor form an "autocrine" system in which the yeast cell expresses a heterologous polypeptide (e.g., a test polypeptide to be evaluated for receptor agonist or antagonist activity) that may stimulate the receptor expressed by that yeast cell. In certain embodiments, the heterologous polypeptide includes a signal sequence that facilitates transport of the polypeptide to a location allowing interaction with the extracellular region of the receptor. For example, the signal sequence corresponds to a leader peptide of the *Saccharomyces cerevisiae* α factor or a-factor. Development and use of this "autocrine" system is described in further detail below.

Preferred yeast host cells of the invention belong to the species *Saccharomyces cerevisiae*. Examples of other suitable yeast host cells are described further in subsection IV below.

The yeast cells expressing a heterologous (e.g., human) receptor can be used in screening assays to identify modulators of the receptor. Accordingly, in one embodiment, the invention provides a method of identifying compounds which modulate a heterologous (e.g., human) receptor (e.g., an IL8 or galanin receptor) expressed by a yeast cell, comprising the steps of:

(i) contacting a mixture of yeast cells of the invention that express a heterologous (e.g., human) receptor with a test compound;

(ii) allowing cells within the mixture to generate a detectable signal; and (iii) identifying the test compound as a modulator of the heterologous (e.g., human) receptor expressed by the yeast cell.

Ways of monitoring changes in a detectable signal in the yeast host cells (e.g., using a reporter gene) are described in detail in other sections of the application. Moreover, types of compounds (e.g., various libraries of compounds) that can be screened using the assay are described in detail in other sections of the application. Examples of screening assays using yeast cells expressing a human G protein coupled receptor are described in detail in the appended Examples.

Standard techniques for preparing recombinant DNA constructs and for manipulating yeast cells and genomes (e.g., by transfection and homologous recombination) can be used to create the receptor-expressing host cells for use in the invention. Exemplary constructs and techniques for making the host cells of the invention are described in further detail in the Examples.

IV. Host Cells

Suitable host cells for generating the subject assay include prokaryotes, yeast, or higher eukaryotic cells, including plant and animal cells, especially mammalian cells. Prokaryotes include gram negative or gram positive organisms. Examples of suitable mammalian host cell lines include the COS-7 line of monkey kidney cells (ATCC CRL 1651) (Gluzman (1981) Cell 23:175) CV-1 cells (ATCC CCL 70), L cells, C127, 3T3, Chinese hamster ovary (CHO), HeLa, HEK-293, SWISS 3T3, and BHK cell lines.

In one embodiment, the host cells are yeast cells. The host cells of the present invention may be of any species of yeast which are cultivatable and in which an exogenous receptor can be made to engage the appropriate signal transduction machinery of the host cell. Exemplary species include *Kluyverei lactis*, *Schizosaccharomyces pombe*, and *Ustilaqo maydis*, with *Saccharomyces cerevisiae* being preferred. Other yeast which can be used in practicing the present invention are *Neurospora crassa*, *Aspergillus niger*, *Aspergillus nidulans*, *Pichiapastoris*, *Candida tropicalis*, and *Hansenula polymorpha*. The term "yeast", as used herein, includes not only yeast in a strictly taxonomic sense, i.e., unicellular organisms, but also yeast-like multicellular fungi or filamentous fungi.

V. Expression Systems

In general, it will be desirable that an expression vector be capable of replication in the host cell. Heterologous DNA may be integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (*Cloning Vectors: A Laboratory Manual*, Elsevier, New York, 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. Suitable promoters for function in yeast include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

In certain embodiments, it will be desirable to control the copy number of the heterologous gene which is expressed. For example, in certain embodiments, expression of a gene (e.g., a receptor gene or a gene which results in activation of the pheromone response pathway) will be from a low copy number in order to better detect ligand induced signaling.

Exemplary low copy number plasmids suitable for use in yeast cells are known in the art and include, e.g., ARS vectors or centromeric sequences (CEN) (See e.g., Romanos et al. 1992. *Yeast* 8:423). In other embodiments, however, the use of high copy number plasmids will be desirable. Exemplary high copy number plasmids are also known in the art and include *E. coli*-yeast shuttle vectors based on 2μ. In yet other embodiments it may be desirable to express heterologous DNA in a yeast cell using integrating vectors, such as YIp vectors. The use of high DNA concentrations of integrating vectors can result in tandem multicopy inserts due to repeated recombination events. Alternatively, heterologous DNA can be integrated into reiterated chromosomal DNA to generate stable multi-copy integrants (Kingsman et al. 1985. *Biotechnol. Genet. Eng. Revs.* 3:377; Lopes et al. 1989. *Gene* 79:199)

VI. Expression of Heterologous Receptors

For expression in yeast, a heterologous G protein coupled receptor gene can be operably linked to a promoter functional in the cell to be engineered and to a signal sequence that also functions in the cell. For example, suitable promoters include Ste2, Ste3 and gal10. Optionally, the codons of the gene can be optimized for expression in yeast. See Hoekema et al.,(1987) *Mol. Cell. Biol.*, 7:2914–24; Sharp, et al., (1986)14:5125–43.

In some instances a foreign receptor which is expressed in yeast will functionally integrate into the yeast membrane, and there interact with the endogenous yeast G protein. In other instances, either the receptor may be modified or a compatible G protein or a chimeric (i.e., part yeast/part mammalian), or a mutant mammalian G protein subunit which can properly interact with the exogenous receptor G protein may be provided. The homology of seven transmembrane domain receptors (STRs) is discussed in Dohlman et al., *Ann. Rev. Biochem.*, (1991) 60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergent. The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites. Such information can be useful in creating mutations in GPCRs to enhance functionality.

If a naturally occurring exogenous GPCR cannot be made functional in yeast, it may be mutated for this purpose. For example, a comparison can be made of the amino acid sequences of the exogenous receptor and of the yeast receptors, and regions of high and low homology identified. Trial mutations can be made to distinguish regions involved in ligand or G protein binding, from those necessary for functional integration in the membrane. The exogenous receptor can then be mutated in the latter region to more closely resemble the yeast receptor, until functional integration was achieved. If this were insufficient to achieve functionality, mutations could next be made in the regions involved in G protein binding. Alternatively, the naturally occurring exogenous GPCR can be mutated to more closely resemble another mammalian receptor that is known to functionally integrate in yeast cells or random mutagenesis can be performed, followed by selection of mutants that can functionally integrate in the yeast cells. Another possible approach for achieving functional integration of the receptor is to make a chimeric receptor (mammalian/yeast)(see e.g., U.S. Pat. No. 5,576,210 issued to Sledziewski et al).

Preferably, the yeast genome is modified so that it is unable to produce the yeast receptors or G proteins which are homologous to the exogenous receptors or exogenous G protein subunits in functional form in order to facilitate assay interpretation. For example, the endogenous G protein subunit(s) is mutated generating, for instance, a temperature sensitive mutant.

In other embodiments, a secretory signal of a yeast protein can be used to direct transport of the heterolgous G protein coupled receptors to the plasma membrane. Previous work has demonstrated the secretory expression of foreign proteins in yeast cells using the signal sequence of a yeast secreted protein such as invertase or acid phosphatase, encoded by the SUC2 and PH05 genes, respectively (Schraber, M. D. et al. (1986) *Methods Enzymol.* 119:416; Moir, D. T. et al. (1991) *Methods Enzymol.* 194:491–507). The vast majority of the secreted proteins possess a hydrophobic N-terminal signal sequence which targets them to the endoplasmic reticulum. A leader sequence of the α-factor precursor encoded by the MFα1 gene was shown to promote the most efficient secretion of various heterologous proteins. In addition to a signal sequence, the α-factor leader includes a hydrophilic pro-region which is believed to facilitate protein transport at the later stages of the secretory pathway.

Both secreted and membrane proteins including G protein-coupled receptors are delivered to the cell surface through the same secretory pathway. Some receptors, for example, metabotropic glutamate receptors and vasoactive intestinal peptide receptors, also possess the N-terminal signal sequence, whereas some do not. In the latter case, a first transmembrane domain is believed to interact with the ER translocation machinery. The use of yeast secretory signals, in particular, the α-factor leader, may be desirable to provide the more efficient integration of the receptors into the membrane of the endoplasmic reticulum and transport to the plasma membrane. In fact, the cell surface expression of the rat M5 receptor directed by the α-factor leader has been documented (Huang et al. (1992) *Biochem. Biophys. Res. Commun.* 181:1180).

VII. G Protein Subunits and Complexes

In certain instances it will be desirable to modify naturally occurring forms of yeast or mammalian G-protein subunits. For instance, where a heterologous GPCR does not adequately couple to the endogenous yeast G protein subunit, such a subunit, e.g., GPA1 may be modified to improve coupling. Such modifications can be made by mutation, e.g., directed mutation or random mutation, using methods known in the art and described in more detail below.

Alternatively, a heterologous subunit can be expressed. The specificity of coupling of a receptor to a heterotrimeric G-protein is largely determined by the a subunit of the G-protein. Thus, in preferred embodiments, a heterologous Gα subunit is expressed in the yeast cell. The predominant role of the yeast Gα, GPA1, is to bind to and sequester the effector-signaling βγ component of the heterotrimer. Thus, in order to achieve functional integration into a yeast pheromone signaling pathway, a heterologous Gα subunit must bind to yeast βγ in the quiescent state, and release it upon receptor activation.

If functional integration is not achieved, or is not optimal, the heterologous subunit can be mutated. For example, in general, mammalian Gα subunits couple poorly to the βγ subunits of yeast cells. In yeast which lack their own endogenous Gα subunit, this failure to couple results in the constitutive activation of the pheromone pathway due to the effector activity of the unbound yeast βγ. Accordingly, if a naturally occurring heterologous G protein subunit does not enhance coupling, modifications can be made. Such modifications may take the form of mutations which are designed to increase the resemblance of the G protein subunit to the yeast G protein subunit while decreasing its resemblance to the heterologous receptor-associated G protein subunit.

For example, a residue may be changed so as to become identical to the corresponding yeast G protein residue, or to belong to the same exchange group of that residue. After modification, the modified G protein subunit might or might not be "substantially homologous" to the heterologous and/ or the yeast G protein subunit.

In the case of Gα, modifications are preferably concentrated in regions of the Gα which are likely to be involved in Gβγ binding.

In other embodiments, modifications will take the form of replacing one or more amino acids of the receptor-associated G protein subunit with the corresponding yeast G protein subunit amino acids, thereby forming a chimeric G protein subunit. In preferred embodiments, three or more consecutive amino acids are replaced. In other embodiments, point mutations may be sufficient.

Chimeric G protein subunits of the invention enhance coupling of the heterologous receptor to the endogenous yeast signaling pathway. For example, a chimeric Gα subunit will interact with the heterologous receptor and the yeast Gβγ complex, thereby permitting signal transduction.

A yeast cell of the present invention can express one or more of the indicated G protein structures. For example, a yeast cell can express a chimeric or mutant Gα subunit, and an endogenous yeast Gβγ, a mammalian Gβγ, a mutated mammalian Gβγ, or a chimeric Gβγ.

In preferred embodiments, both the receptor and the heterologous subunit are derived from the same source, e.g., are mammalian. In particularly preferred embodiment, both are human in origin.

In another preferred embodiment, a yeast cell that expresses a heterologous or chimeric G protein subunit has been modified such that the endogenous, homologous G protein subunit gene is disrupted.

In certain embodiments, yeast strains lacking pheromone receptors and having no heterologous receptor capable of coupling to the pheromone response pathway may be used to assess the affinity of an endogenous yeast G protein subunit, a mammalian G protein subunit, a mutated G protein subunit, or chimeric G protein subunit for other yeast subunits. For example, the affinity of GPA1p, chimeric GPA-Gα s, or other Gα subunit for yeast βγ or other chimeric βγ subunit can be assessed. Such strains depend on free βγ for signaling through the pheromone response pathway leading to growth arrest. Mutant Gα subunits may be tested in such a system, those which bind βγ more effectively will sequester βγ and reduce or block signaling. Preferably, such chimeras and GPA1 subunits can be assessed in a gpa1⁻ background to avoid competition with GPA1 for βγ. For example, Gα s chimeric mutants (see below) carrying D229S, E10K, N254D, or S286P were found to sequester βγ more effectively than the mutant with wild type sequences. Also, double mutants were even more effective than either single mutant. Similarly, overexpression of Gαs by driving transcription from the highly efficient PGK promoter resulted in dampening of the receptor coupling which may be offset by introduction of the double mutant Gαs (D229S, E10K).

Guidance for making mutations in G protein subunits and in the construction of chimeric G protein subunits is provided below.

Site-Directed Mutagenesis Versus Random Mutagenesis

There are numerous art recognized ways to solve the structure-function problems of the sort presented by attempts to define the determinants involved in mediating the association of the subunits that comprise the G protein heterotrimer. For example, in one approach, discussed above with respect to hybrid constructs, specific mutations or alterations are introduced into a molecule based upon the available experimental evidence. In a second approach, random mutagenesis techniques, coupled with selection or screening systems, are used to introduce large numbers of mutations into a molecule, and that collection of randomly mutated molecules is then subjected to a selection for the desired phenotype or a screen in which the desired phenotype can be observed against a background of undesirable phenotypes.

With random mutagenesis one can mutagenize an entire molecule or one can proceed by cassette mutagenesis. In the former instance, the entire coding region of a molecule is mutagenized by one of several methods (chemical, PCR, doped oligonucleotide synthesis) and that collection of randomly mutated molecules is subjected to selection or screening procedures. Random mutagenesis can be applied in this way in cases where the molecule being studied is relatively small and there are powerful and stringent selections or screens available to discriminate between the different classes of mutant phenotypes that will inevitably arise. In the second approach, discrete regions of a protein, corresponding either to defined structural (i.e. α-helices, β-sheets, turns, surface loops) or functional determinants (e.g., catalytic clefts, binding determinants, transmembrane segments) are subjected to saturating or semi-random mutagenesis and these mutagenized cassettes are re-introduced into the context of the otherwise wild type allele.

Cassette mutagenesis is most useful when there is experimental evidence available to suggest a particular function for a region of a molecule and there is a powerful selection and/or screening approach available to discriminate between interesting and uninteresting mutants. Cassette mutagenesis is also useful when the parent molecule is comparatively large and the desire is to map the functional domains of a molecule by mutagenizing the molecule in a step-wise fashion, i.e. mutating one linear cassette of residues at a time and then assaying for function.

The present invention provides for applying random mutagenesis in order to further delineate the determinants involved in Gα-Gβγ or subunit-receptor association. Random mutagenesis may be accomplished by many means, including:

1. PCR mutagenesis, in which the error prone Taq polymerase is exploited to generate mutant alleles of G protein subunits, which are assayed directly in yeast for an ability to couple.

2. Chemical mutagenesis, in which expression cassettes encoding G protein subunits are exposed to mutagens and the protein products of the mutant sequences are assayed directly in yeast for an ability to couple.

3. Doped synthesis of oligonucleotides encoding portions of the G protein subunit gene.

4. In vivo mutagenesis, in which random mutations are introduced into the coding region of G protein subunits by passage through a mutator strain of E. coli, XL 1-Red (mutD5 mutS mutT) (Stratagene, Menasa, Wis.).

In certain embodiments, for example, the random mutagenesis may be focused on regions suspected to be involved in Gα-Gβγ association. Random mutagenesis approaches are feasible for two reasons. First, in yeast one has the ability to construct stringent screens and facile selections (growth vs. death, transcription vs. lack of transcription) that are not readily available in mammalian systems. Second, when using yeast it is possible to screen efficiently through thousands of transformants rapidly. For example, this relatively small region of Gα subunits represents a reasonable target for cassette mutagenesis. Another region that may be amenable to cassette mutagenesis is that defining the surface of the switch region of Gαt subunits that is solvent-exposed in the crystal structures of Gαi and transducin. From the data described below, this surface may contain residues that are in direct contact with yeast Gβγ subunits, and may therefore be a reasonable target for mutagenesis.

A. Modification of Gα

Some aspects of Gα structure are relevant to the design of modified Gα subunits. Alignments of Gα and GPA1 can be made to determine sequence similarity. For alignments of the entire coding regions of GPA1 with Gαs, Gαi, and GαO, Gαq and Gαz, see Dietzel and Kurjan (1987, *Cell* 50:573) and Lambright, et al. (1994, *Nature* 369:621–628). Additional sequence information is provided by Mattera, et al. (1986, *FEBS Lett* 206:36–41), Bray, et al. (1986, *Proc. Natl. Acad. Sci USA* 83:8893–8897) and Bray, et al. (1987, *Proc Natl. AcadSci USA* 84:5115–5119). An alignment of GPA1 and four other Gα proteins is provided by Stone and Reed (1990. Mol. Cell Biol. 10:4439).

The gene encoding a G protein homolog of *S. cerevisiae* was cloned independently by Dietzel and Kurjan (supra) (who referred to the gene as SCG1) and by Nakafuku, et al. (1987 *Proc Natl Acad Sci* 84:2140–2144) (who called the gene GPA1). Sequence analysis revealed a high degree of homology between the protein encoded by this gene and mammalian Gα. GPA1 encodes a protein of 472 amino acids, as compared with approximately 340–350 amino acids for most mammalian Gα subunits in four described families, Gαs, Gαi, Gαq and Gα12/13. Nevertheless, GPA1 shares overall sequence and structural homology with all Gα proteins identified to date. The highest overall homology in GPA1 is to the Gαi family (48% identity, or 65% with conservative substitutions) and the lowest is to Gαs (33% identity, or 51% with conservative substitutions) (Nakafuku, et al., supra).

The regions of high sequence homology among Gα subunits are dispersed throughout their primary sequences, with the regions sharing the highest degree of homology mapping to sequence that comprises the guanine nucleotide binding/GTPase domain. This domain is structurally similar to the αβ fold of ras proteins and the protein synthesis elongation factor EF-Tu. This highly conserved guanine nucleotide-binding domain consists of a six-stranded β sheet surrounded by a set of five α-helices. It is within these β sheets and a helices that the highest degree of conservation is observed among all Gα proteins, including GPA1. The least sequence and structural homology is found in the intervening loops between the β sheets and α helices that define the core GTPase domain. There are a total of four "intervening loops" or "inserts" present in all Gα subunits. In the crystal structures reported to date for the GDP- and GTPγS-liganded forms of bovine rod transducin (Noel, et al. (1993) *Nature* 366:654–663); (Lambright, et al. (1994) *Nature* 369:621–628), the loop residues are found to be outside the core GTPase structure. Functional roles for these loop structures have been established in only a few instances. A direct role in coupling to phosphodiesterase-γ has been demonstrated for residues within inserts 3 and 4 of Gαt (Rarick, et al. (1992) *Science* 256:1031–1033); (Artemyev, et al. (1992) *J. Biol. Chem.* 267:25067–25072), while a "GAP-like" activity has been ascribed to the largely α-helical insert 1 domain of GαS (Markby, et al. (1993) *Science* 262:1805–1901).

While the amino- and carboxy-termini of Gα subunits do not share striking homology either at the primary, secondary, or tertiary levels, there are several generalizations that can be made about them. First, the amino termini of Gα subunits have been implicated in the association of Gα with Gβγ complexes and in membrane association via N-terminal myristoylation. In addition, the carboxy-termini have been implicated in the association of Gαβγ heterotrimeric complexes with G protein-coupled receptors (Sullivan, et al. (1987) *Nature* 330:758–760); West, et al. (1985) *J. Biol. Chem.* 260:14428–14430); (Conklin, et al. (1993) *Nature* 363:274–276); (Kallal and Kurjan. 1997. *Mol. Cell. Biol.* 17:2897). Data in support of these generalizations about the function of the N-terminus derive from several sources, including both biochemical and genetic studies.

In the GPA$_{41}$Gα hybrids, the amino terminal 41 residues are derived from GPA1. All residues following position 41 are contributed by the human Gα subunits, including the consensus nucleotide binding motif. For alignments of the entire coding regions of GPA1 with Gαs, Gαi, and GαO, Gαq and Gαz, see Dietzel and Kurjan (1987, *Cell* 50:573) and Lambright, et al. (1994, *Nature* 369:621–628). Additional sequence information is provided by Mattera, et al. (1986, *FEBS Lett* 206:36–41), Bray, et al. (1986, *Proc. Natl. Acad. Sci USA* 83:8893–8897) and Bray, et al. (1987, *Proc Natl. Acad Sci USA* 84:5115–5119).

There is little if any sequence homology shared among the amino termini of Gα subunits. The amino terminal domains of Gα subunits that precede the first β-sheet vary in length from 41 amino acids (GPA1) to 31 amino acids (Gαt). Most Gα subunits share the consensus sequence for the addition of myristic acid at their amino termini, although not all Gα subunits that contain this motif have myristic acid covalently associated with the glycine at position 2 (Speigel, et al. (1991) *TIBS* 16:338–3441). The role of this post-translational modification has been inferred from studies in which the activity of mutant Gα subunits from which the consensus sequence for myristoylation has been added or deleted has been assayed (Mumby et al. (1990) *Proc. Natl. Acad. Sci. USA* 87: 728–732; (Linder, et al. (1991) *J. Biol Chem.* 266:4654–4659); Gallego, et al. (1992) *Proc. Natl. Acad. Sci. USA* 89:9695–9699). These studies suggest two roles for N-terminal myristoylation. First, the presence of amino-terminal myristic acid has in some cases been shown to be required for association of Gα subunits with the membrane, and second, this modification has been demonstrated to play a role in modulating the association of Gα subunits with Gβγ complexes. The role of myristoylation of the GPA1 gene products, at present is unknown.

In other biochemical studies aimed at examining the role of the amino-terminus of Gα in driving the association between Gα and Gβγ subunits, proteolytically or genetically truncated versions of Gα subunits were assayed for their ability to associate with Gβγ complexes, bind guanine nucleotides and/or to activate effector molecules. In all cases, Gα subunits with truncated amino termini were deficient in all three functions (Graf, et al. (1992) *J. Biol. Chem.* 267:24307–24314); (Journot, et al. (1990) *J. Biol. Chem.* 265:9009–9015); and (Neer, et al. (1988) *J. Biol.*

Chem 263:8996–9000). Slepak, et al. (1993, *J. Biol. Chem.* 268:1414–1423) reported a mutational analysis of the N-terminal 56 a.a. of mammalian Gαo expressed in *Escherichia coli*. Molecules with an apparent reduced ability to interact with exogenously added mammalian Gβγ were identified in the mutant library. As the authors pointed out, however, the assay used to screen the mutants the extent of ADP-ribosylation of the mutant Gα by pertussis toxin was not a completely satisfactory probe of interactions between Gα and Gβγ. Mutations identified as inhibiting the interaction of the subunits, using this assay, may still permit the complexing of Gα and Gβγ while sterically hindering the ribosylation of Gα by toxin. Other work has revealed specific amino acid residues of GPA1 that are important in GPA1 function. For example, a E307K mutation appears to create an α subunit with a broadened specificity for Gβ subunits (Whiteway et al. 1994. Mol. Cell. Biol. 14:3223). Interestingly, the residue in the mammalian Gα subunit which is equivalent to the E307 position is diagnostic for a particular class of mammalian α subunits. For example, the $G_s\alpha$ subunits contain a lysine at this position, the $G_o$ and $G_i\alpha$ subunits contain a histidine, the transducin αu subunits have a glutimine, the Gq α subunits have a proline, and the $G_{13}$ α subunits have an aspartic acid at this site (Whiteway et al. supra).

Genetic studies examined the role of amino-terminal determinants of Gα in heterotrimer subunit association have been carried out in both yeast systems using GPA1-mammalian Gα hybrids (Kang, et al. (1990) *Mol. Cell. Biol.* 10:2582–2590) and in mammalian systems using Gαi/Gαs hybrids (Russell and Johnson (1993) *Mol. Pharmacol.* 44:255–263). In the former studies, gene fusions, composed of yeast GPA1 and mammalian Gα sequences were constructed by Kang, et al. (supra) and assayed for their ability to complement a gpa1 null phenotype (i.e., constitutive activation of the pheromone response pathway) in *S. cerevisiae*. Kang, et al. demonstrated that wild type mammalian Gαs, Gαi but not Gαo proteins are competent to associate with yeast Gα and suppress the gpa1 null phenotype, but only when overexpressed. Fusion proteins containing the amino-terminal 330 residues of GPA1 sequence linked to 160, 143, or 142 residues of the mammalian Gαs, Gαi and Gαo carboxyl-terminal regions, respectively, also coupled to the yeast mating response pathway when overexpressed on high copy plasmids with strong inducible (CUP) or constitutive (PGK) promoters. All three of these hybrid molecules were able to complement the gpa1 null mutation in a growth arrest assay, and were additionally able to inhibit α-factor responsiveness and mating in tester strains. These last two observations argue that hybrid yeast-mammalian Gα subunits are capable of interacting directly with yeast Gβγ, thereby disrupting the normal function of the yeast heterotrimer. Fusions containing the amino terminal domain of Gαs, Gαi or Gαo, however, did not complement the gpa1 null phenotype, indicating a requirement for determinants in the amino terminal 330 amino acid residues of GPA1 for association and sequestration of yeast Gβγ complexes. Taken together, these data suggest that determinants in the amino terminal region of Gα subunits determine not only the ability to associate with Gβγ subunits in general, but also with specific Gβγ subunits in a species-restricted manner.

Hybrid Gαi/Gαs subunits have been assayed in mammalian expression systems (Russell and Johnson (supra). In these studies, a large number of chimeric Gα subunits were assayed for an ability to activate adenylyl cyclase, and therefore, indirectly, for an ability to interact with Gβγ (i.e., coupling of Gα to Gβγ=inactive cyclase; uncoupling of Gα from Gβγ=active cyclase). From these studies a complex picture emerged in which determinants in the region between residues 25 and 96 of the hybrids were found to determine the state of activation of these alleles as reflected in their rates of guanine nucleotide exchange and GTP hydrolysis and the extent to which they activated adenylyl cyclase in vivo. These data could be interpreted to support the hypothesis that structural elements in the region between the amino terminal methionine and the βsheet identified in the crystal structure of Gαt (see Noel, et al. supra and Lambright, et al. supra) are involved in determining the state of activity of the heterotrimer by (1) driving association/dissociation between Gα and Gβγ subunits; (2) driving GDP/GTP exchange. While there is no direct evidence provided by these studies to support the idea that residues in this region of Gα and residues in Gβγ subunits contact one another, the data nonetheless provide a positive indication for the construction of hybrid Gα subunits that retain function. There is, however, a negative indicator that derives from this work in that some hybrid constructs resulted in constitutive activation of the chimeric proteins (i.e., a loss of receptor-dependent stimulation of Gβγ dissociation and effector activation).

B. Construction of Chimeric Gα Subunits.

In preferred embodiments chimeric Gα subunits retain as much of the sequence of the native mammalian proteins as possible and, in particularly preferred embodiments, the level of expression for the heterologous components should approach, as closely as possible, the level of their endogenous counterparts. The results described by King, et al. (1990, Science 250:121–123) for expression of the human β2-adrenergic receptor and Gαs in yeast, taken together with negative results obtained by Kang, et al. (supra) with full-length mammalian Gα subunits other than Gαs, led to the following preferred embodiments for the development of yeast strains in which mammalian G protein-coupled receptors could be linked to the pheromone response pathway.

In one embodiment, mammalian Gα subunits are expressed using the native sequence of each subunit or, alternatively, as minimal gene fusions with sequences from the amino-terminus of GPA1 replacing the homologous residues from the mammalian Gα subunits. In another embodiment, mammalian Gα subunits are expressed from the GPA1 promoter either on low copy plasmids or after integration into the yeast genome as a single copy gene. In certain embodiments, endogenous Gβγ subunits are provided by the yeast STE4 and STE18 loci, while in other embodiments chimeric or heterologous Gβ and/or Gγ subunits are also provided.

C. Rational Design of Chimeric Gα Subunits

Several classes of rationally designed GPA1-mammalian Gα hybrid subunits have been tested for the ability to couple to yeast βγ. The first, and largest, class of hybrids are those that encode different lengths of the GPA1 amino terminal domain in place of the homologous regions of the mammalian Gα subunits. This class of hybrid molecules includes $GPA_{BAMH1}$, $GPA_{41}$, $GPA_{ID}$, and $GPA_{LW}$ hybrids, described below. The rationale for constructing these hybrid Gα proteins is based on results, described above, that bear on the importance of the amino terminal residues of Gα in mediating interaction with Gβγ.

Preferably, the yeast Gα subunit is replaced by a chimeric Gα subunit in which a portion, e.g., at least about 20, more preferably at least about 40, amino acids, from the amino terminus of the yeast Gα is fused to a sequence from a mammalian (or other exogenous) Gα. While about 40 amino acids is the suggested starting point, shorter or longer portions may be tested to determine the minimum length required for coupling to yeast Gβγ and the maximum length compatible with retention of coupling to the exogenous receptor. It is presently believed that only the final 10 or 20 amino acids at the carboxy terminus of the Gα subunit are required for interaction with the receptor.

i. GPA$_{BAMH1}$ Hybrids.

Kang et al. supra. described hybrid Gα subunits encoding the amino terminal 310 residues of GPA1 fused to the carboxyl terminal 160, 143 and 142 residues, respectively, of GαS, Gαi2, and Gαo. In all cases examined by Kang et al., the hybrid proteins were able to complement the growth arrest phenotype of gpal strains. Hybrids between GPA1 and Gαi3, Gαq and Gα16 can be constructed, as described below, and functionally complement the growth arrest phenotype of gpal strains.

GPA41 hybrids: The rationale for constructing a minimal hybrid encoding only 41 amino acids of GPA1 relies upon the biochemical evidence for the role of the amino-terminus of Gα subunits discussed above, together with the following observation. Gβ and Gγ subunits are known to interact via α-helical domains at their respective amino-termini (Pronin, et al. (1992) *Proc. Natl. Acad. Sci. USA* 89:6220–6224); Garritsen, et al. 1993). The suggestion that the amino termini of Gα subunits may form an helical coil and that this helical coil may be involved in association of Gα with Gβγ (Masters et al (1986) *Protein Engineering* 1:47–54); Lupas et al.(1992) *FEBS Lett.* 314:105–108) leads to the hypothesis that the three subunits of the G-protein heterotrimer interact with one another reversibly through the winding and unwinding of their amino-terminal helical regions. (For further description of the crystal structure of G proteins, and subunits thereof, see Lambright et al. (1996) *Nature* 379: 311–319 and Sondek et al. (1996) *Nature* 379:369–374.) A mechanism of this type has been suggested, as well, from an analysis of leucine zipper mutants of the GCN4 transcription factor (Harbury, et al. (1993) *Science* 262:1401–1407). The rationale for constructing hybrids like those described by Kang, et al. supra., that contain a majority of yeast sequence and only minimal mammalian sequence, derives from their ability to function in assays of coupling between Gα and Gβγ subunits. However, these chimeras had never been assayed for an ability to couple to both mammalian G protein-coupled receptors and yeast Gβγ subunits, and hence to reconstitute a hybrid signaling pathway in yeast.

GPA$_{41}$ hybrids that have been constructed and tested include Gαs, Gαi2, Gαi3, Gαq, Gαo$_a$, Gαo$_b$ and Gα16. Hybrids of Gαs, Gαi2, Gαi3, and Gα16 functionally complement the growth arrest phenotype of gpa1 strains, while GPA$_{41}$ hybrids of Gαo$_a$ and Gαo$_b$ do not. In addition to being tested in a growth arrest assay, these constructs have been assayed in the more sensitive transcriptional assay for activation of a fus1p-HIS3 gene. In both of these assays, the GPA$_{41}$-Gαs hybrid couples less well than the GPA$_{41}$-i2, -i3, and -16 hybrids, while the GPA$_{41}$-o$_a$, and -o$_b$ hyrids do not function in either assay.

Several predictive algorithms indicate that the amino terminal domain up to the highly conserved sequence motif LLLLGAGESG (SEQ ID NO:6) (the first L in this motif is residue 43 in GPA1) forms a helical structure with amphipathic character. Assuming that a heptahelical repeat unit, the following hybrids between yeast GPA1 and mammalian GαS can be used to define the number of helical repeats in this motif necessary for hybrid function:

GPA1-7/Gαs8-394
GPA1-14/Gαs15-394
GPA1-21/Gαs22-394
GPA1-28/Gαs29-394
GPA1-35/Gαs36-394
GPA1-42/Gαs43-394

In these hybrids, the prediction is that the structural repeat unit in the amino terminal domain up to the tetra-leucine motif is 7, and that swapping sequences in units of 7 will in effect amount to a swap of unit turns of turns of the helical structure that comprises this domain.

A second group of "double crossover" hybrids of this class are those that are aligned on the first putative heptad repeat beginning with residue G11 in GPA1. In these hybrids, helical repeats are swapped from GPA1 into a GαS backbone one heptad repeat unit at a time.

GαS1-10/GPA11-17/Gαs18-394
GαS1-17/GPA18-24/GαS25-394
GαS1-17/GPA25-31/GαS32-394
GαS1-17/GPA32-38/GαS39-394

The gap that is introduced between residues 9 and 10 in the GαS sequence is to preserve the alignment of the LLLLGAGE (SEQ ID NO:7) sequence motif. This class of hybrids can be complemented by cassette mutagenesis of each heptad repeat followed by screening of these collections of "heptad" libraries in standard coupling assays.

A third class of hybrids based on the prediction that the amino terminus forms a helical domain with a heptahelical repeat unit are those that effect the overall hydrophobic or hydrophilic character of the opposing sides of the predicted helical structure (See Lupas et al. supra). In this model, the a and d positions of the heptad repeat abcdefg are found to be conserved hydrophobic residues that define one face of the helix, while the e and g positions define the charged face of the helix. In this class of hybrids, the sequence of the GαS parent is maintained except for specific substitutions at one or more of the following critical residues to render the different helical faces of GαS more "GPA1-like"

K8Q
+I-10
E10G
Q12E
R13S
N14D
E15P
E15F
K17L
E21R
K28Q
K32L
V36R

This collection of single mutations could be screened for coupling efficiency to yeast Gβγ and then constructed in combinations (double and greater if necessary).

A fourth class of hybrid molecules that span this region of GPA1-Gα hybrids are those that have junctions between GPA1 and Gα subunits introduced by three primer PCR. In this approach, the two outside primers are encoded by sequences at the initiator methionine of GPA1 on the 5' side and at the tetraleucine motif of GαS (for example) on the 3' side. A series of junctional primers spanning different junctional points can be mixed with the outside primers to make a series of molecules each with different amounts of GPA1 and GαS sequences, respectively.

ii. GPA$_{ID}$ and GPA$_{LW}$ hybrids.

The regions of high homology among Gβγ subunits that have been identified by sequence alignment are interspersed throughout the molecule. The GI region containing the highly conserved GSGESGDST (SEQ ID NO:8) motif is followed immediately by a region of very low sequence conservation, the "i1" or insert 1 region. Both sequence and length vary considerably among the i1 regions of the Gα subunits. By aligning the sequences of Gα subunits, the conserved regions bounding the i1 region were identified and two additional classes of GPA1-Gα hybrids were constructed. The $GPA_{ID}$ hybrids encode the amino terminal 102 residues of GPA1 (up to the sequence QARKLGIQ)(SEQ ID NO:9) fused in frame to mammalian Gα subunits, while the $GPA_{LW}$ hybrids encode the amino terminal 244 residues of GPA1. The reason for constructing the $GPA_{ID}$ and $GPA_{LW}$ hybrids was to test the hypothesis that the i1 region of GPA1 is required for mediating the interaction of GPA1 with yeast Gβγ subunits, for the stable expression of the hybrid molecules, or for function of the hybrid molecules. The $GPA_{ID}$ hybrids contain the amino terminal domain of GPA1 fused to the i1 domain of mammalian subunits, and therefore do not contain the GPA1 i1 region, while the $GPA_{LW}$ hybrids contain the amino terminal 244 residues of GPA1 including the entire i1 region (as defined by sequence alignments). Hybrids of both $GPA_{ID}$ and $GPA_{LW}$ classes were constructed for GαS, C-αi2, Gαi3, $Gαo_a$, and Gα16; none of these hybrids complemented the gpa1 growth arrest phenotype.

Subsequent to the construction and testing of the $GPA_{ID}$ and $GPA_{LW}$ classes of hybrids, the crystal structures of $G_{transducin}$ in both the GDP and GTPγS-liganded form, and the crystal structure of several Gαi1 variants in the GTPγS-liganded and GDP-AIF$_4$ forms were reported (Noel et al. supra; Lambright et al. supra; and Coleman et al.(1994) Science 265:1405–1412). The crystal structures reveal that the i1 region defined by sequence alignment has a conserved structure that is comprised of six alpha helices in a rigid array, and that the junctions chosen for the construction of the $GPA_{ID}$ and $GPA_{LW}$ hybrids were not compatible with conservation of the structural features of the i1 region observed in the crystals. The junction chosen for the $GPA_{ID}$ hybrids falls in the center of the long αA helix; chimerization of this helix in all likelihood destabilizes it and the protein structure in general. The same is true of the junction chosen for the $GPA_{LW}$ hybrids in which the crossover point between GPA1 and the mammalian Gα subunit falls at the end of the short αC helix and therefore may distort it and destabilize the protein.

The failure of the $GPA_{ID}$ and $GPA_{LW}$ hybrids is predicted to be due to disruption of critical structural elements in the i1 region as discussed above. Based upon new alignments and the data presented in Noel et al (supra), Lambright et al (supra), and Coleman et al (supra), this problem can be averted with the ras-like core domain and the i1 helical domain are introduced outside of known structural elements like alpha-helices.

Hybrid A GαS1-67/GPA66-299/GαS203-394
This hybrid contains the entire i1 insert of GPA1 interposed into the GαS sequence.
Hybrid B GPA1-41/GαS4443-67/GPA66-299/GαS203-394
This hybrid contains the amino terminal 41 residues of GPA1 in place of the 42 amino terminal residues of GαS found in Hybrid A.

iii. Gαs Hybrids.

There is evidence that the "switch region" encoded by residues 171–237 of Gα transducin (using the numbering of (Noel et al (supra)) also plays a role in Gβγ coupling. First, the G226A mutation in GαS prevents the GTP-induced conformational change that occurs with exchange of GDP for GTP upon receptor activation by ligand. This residue maps to the highly conserved sequence DVGGQ, (SEQ ID NO:10) present in all Gα subunits and is involved in GTP hydrolysis. In both the Gαt and Gα i1 crystal structures, this sequence motif resides in the loop that connects the β3 sheet and the α2 helix in the guanine nucleotide binding core. In addition to blocking the conformational change that occurs upon GTP binding, this mutation also prevents dissociation of GTP-liganded Gαs from Gβγ. Second, crosslinking data reveals that a highly conserved cysteine residue in the α2 helix (C215 in Gαo, C210 in Gαt) can be crosslinked to the carboxy terminal region of Gβ subunits. Finally, genetic evidence (Whiteway et al. (1993) Mol Cell Biol. 14:3233–3239) identifies an important single residue in GPA1 (E307) in the β2 sheet of the core structure that may be in direct contact with βγ. A mutation in the GPA1 protein at this position suppresses the constitutive signaling phenotype of a variety of STE4 (Gβ) dominant negative mutations that are also known to be defective in Gα-Gβγ association (as assessed in two-hybrid assay in yeast as well as by more conventional genetic tests).

The GPA1 switch region suppresses coupling to yeast Gβγ (SGS), while in the context of the GPA1 amino terminus the GPA1 switch region stabilizes coupling with Gβγ (GPβγ-SGS). This suggests that these two regions of GPA1 collaborate to allow interactions between Gα subunits and Gβγ subunits. This conclusion is somewhat mitigated by the observation that the $GPA_{41}$-Gαs hybrid that does not contain the GPA1 switch region is able to complement the growth arrest phenotype of gpa1 strains.

The role of the surface-exposed residues of this region may be crucial for effective coupling to yeast Gβγ, and can be incorporated into hybrid molecules as follows below.

GαS-GPA-Switch GαS 1-202/GPA298-350/GαS 253-394
This hybrid encodes the entire switch region of GPA1 in the context of GαS.

GαS-GPA-α2 GQS 1-226/GPA322-332/GQS 238-394
This hybrid encodes the a$_2$ helix of GPA1 in the context of GαS.

GPA41-GαS-GPA-α2GPA1-41/GQS43-226/GPA322-332/GQS238-394
This hybrid encodes the 41 residue amino terminal domain of GPA1 and the α2 helix of GPA1 in the context of GαS.

In addition, hybrids that alter the surface exposed residues of the β2 and β3 sheets of αS so that they resemble those of the GPA1 QS helix can be made. These altered α2 helical domains have the following structure. (The positions of the altered residues correspond to GαS.)

L203K
K211E
D215G
K216S
D229S

These single mutations can be engineered into a GαS backbone singly and in pairwise combinations. In addition, they can be introduced in the context of both the full length GαS and the $GPA_{41}$-GαS hybrid described previously. All are predicted to improve the coupling of Gα subunits to yeast Gβγ subunits by virtue of improved electrostatic and hydrophobic contacts between this region and the regions of Gβ defined by Whiteway and co-workers (Whiteway et al (supra) that define site(s) that interact with GPA1).

In summary, the identification of hybrid Gα subunits that couple to the yeast pheromone pathway has led to the following general observations. First, $GPA_{BAMHI}$ hybrids associate with yeast Gβγ, therefore at a minimum these hybrids contain the determinants in GPA1 necessary for coupling to the pheromone response pathway. Second, the amino terminal 41 residues of GPA1 contain sufficient determinants to facilitate coupling of Gα hybrids to yeast Gβγ in some, but not all, instances, and that some Gα subunits contain regions outside of the first 41 residues that are sufficiently similar to those in GPA1 to facilitate interaction with GPA1 even in the absence of the amino terminal 41 residues of GPA1. Third, there are other determinants in the first 310 residues of GPA1 that are involved in coupling Gα subunits to yeast Gβγ subunits.

The various classes of hybrids noted above are not mutually exclusive. For example, a GPA1 containing GPA1-$_{41}$ could also feature the L203K mutation.

While, for the sake of simplicity, hybrids of yeast GPA1 and a mammalian Gαs have been described here, it will be appreciated that hybrids may be made of other yeast Gα subunits and/or other mammalian Gα subunits, notably mammalian Gαi subunits. Moreover, while the described hybrids are constructed from two parental proteins, hybrids of three or more parental proteins are also possible.

As shown in the Examples, chimeric Gα subunits have been especially useful in coupling receptors to Gαi species.

iv. Expression of Gα

Kang et al. supra reported that several classes of native mammalian Gα subunits were able to interact functionally with yeast α subunits when expression of Gα was driven from a constitutively active, strong promoter (PGK) or from a strong inducible promoter (CUP). These authors reported that rat GαS, Gαi2 or Gαo expressed at high level coupled to yeast βγ. High level expression of mammalian Gα (i.e. non-stoichiometric with respect to yeast βγ) is not preferred for uses like those described in this application. Reconstruction of G protein-coupled receptor signal transduction in yeast requires the signaling component of the heterotrimeric complex (Gβγ) to be present stoichiometrically with Gα subunits. An excess of Gα subunits (αS was required for coupling of mammalian Gαi2 and Gαo to yeast Gβγ in Kang et al.) would dampen the signal in systems where Gβγ subunits transduce the signal. An excess of Gα subunits raises the background level of signaling in the system. Preferably, levels of Gα and Gβγ subunits are balanced. For example, heterologous Gα subunits may be expressed from a low copy (CEN ARS) vector containing the endogenous yeast GPA1 promoter and the GPA1 3' untranslated region. The minimum criterion, applied to a heterologous Gα subunit with respect to its ability to couple functionally to the yeast pheromone pathway, is that it complement a gpa1 genotype when expressed from the GPA1 promoter on low copy plasmids or from an integrated, single copy gene. In the work described in this application, heterologous Gα subunits have been assayed in two biological systems. In the first assay heterologous Gα subunits are tested for an ability to functionally complement the growth arrest phenotype of gpa1 strains. In the second assay the transcription of a fus1-HIS3 reporter gene is used to measure the extent to which the pheromone response pathway is activated, and hence the extent to which the heterologous Gα subunit sequesters the endogenous yeast Gβγ complex. Mammalian Gαs, Gαi2, Gαi3, Gαq, Gα11, Gα16, Gαo$_a$, Gαo$_b$, and Gαz from rat, murine or human origins were expressed from a low copy, CEN ARS vector containing the GPA1 promoter. Functional complementation of gpa1 strains was not observed in either assay system with any of these full-length Gα constructs with the exception of rat and human GαS.

D. Chimeric Yeast βγ Subunits

In addition to or in place of modifying G protein Gα subunits, yeast or heterologous Gβ or Gγ subunits can be modified. The methods described above with regard to Gα modification can be used to alter either or both of these subunits as well. For example, alignments of the yeast sequence and heterologous sequences can be made and combined with information regarding important functional domains. Such information can then be used to provide guidance in making mutations in yeast or heterologous sequences. Likewise, chimeric Gα or Gγ molecules can be constructed to enhance the coupling of heterologous GPCRs to a yeast pheromone signaling pathway.

The yeast STE4 and STE18 are related to the metazoan G protein β and γ subunits, respectively (Whiteway et al. 1989. Cell. 56:467). The β and γ subunits must be capable of interaction with one another as well as with the α subunit and with the effector. Previous work has suggested that mammalian β or γ subunits are divergent enough from their yeast homologues that they cannot functionally replace STE4 or STE 18. (Coria et al. 1996. Yeast. 12:41). Thus, in preferred embodiments, modifications are made to heterologous Gβ or Gγ subunits expressed in yeast and/or chimeric subunits are made to enhance heterologous receptor coupling.

The primary structure of G-protein β subunits is highly conserved from yeast to humans; Ste4 shares approximately 40% identity with human Gβ isoforms (Leberer et al. 1992 EMBO Journal 11:4085). STE4 and the Gβs are 420, and 340 or 341 amino acids long, respectively, and belong to the family of proteins with WD-40 motifs (van der Voorn and Ploegh. 1992. FEBs Lett. 307:131). These motifs can be used to divide Gβ and STE4 into eight blocks (Coria et al. Yeast 1996. 12:41). Among the mammalian Gβs, some have been found to exhibit Gγ subunit selectivity (Pronin and Gautham. 1992. Proc. Natl. Acad. Sci. USA 89:6220; Schmidt et al. 1992. J. Biol. Chem. 267:13807; Kleuss et al. 2. Nature. 358:424). An alignment of the metazoan and yeast G protein β subunits is provided by Corai et al. (1996. Yeast. 12:41). Such an alignment can be used to provide guidance for making mutations to G protein β subunits as described for Gα above. In addition, certain regions of STE4 have been found to be important and thus, may be less amenable to manipulation than other portions of the polypeptide. For example, the c-terminus of the STE4 product is essential for downstream signaling (Coria et al. 1995. FEBS Letters 367:122). Mutations to two small regions in the amino terminal half of Ste4 have also been shown to inhibit signaling (Leberer et al. supra). Mutations which influence the interaction of STE4 and GPA1 have also been identified; mutations to the second copy of the WD40 repeat can be modified to reduce the interaction between STE4 and GPA1, without influencing other aspects of STE4 function (Whiteway et al. 1994. Mol. Cell. Biol. 14:3223)

The Gγs, including STE18, diverge more strongly from each other than do the Gβs. Even among the mammalian G protein γ subunits, there is a fair amount of divergence. The γ subunit may determine the functional specificity of the βγ subunit complex. Complete cDNAs for the γ1 subunit from bovine retina (Hurley et al. Proc. Nat'l Acad. Sci USA. 1984. 81:6948) the γ1, γ3, and γ7 subunits from bovine brain (Robishaw et al. J. Biol. Chem. 1989. 264:15758; Gautam et al. Science. 1989. 244:971; Gautam et al. Proc. Nat'l Acad. Sci. USA. 1990 87:7973; Cali et al. J. Biol. Chem. 1992. 267:24023), and the γ5 subunit from bovine and rat liver (Gisher et al. 1992. 12:1585) have been reported.

The STE18 gene of yeast terminates with a CAAX box (where A is an aliphatic amino acid, and X is any uncharged amino acid). This sequence is involved in prenylation of Gγ and is likely important in the localization of Gγ to the membrane and may, thus, be less amenable to manipulation than other portions of the sequence. (Kurjan. 1992. Ann. Rev. Biochem. 61:1097). Saturation mutagenesis has also provided insight into regions of STE18 that are important in STE18 function. Mutations in STE18 which compensate for mutations in STE4 were identified at serine 65, threonine 71, and valine 80. Dominant negative alleles of the STE18 gene were also identified (Whiteway et al. 1992. Biochem. Cell. Biol. 70:1230). These truncated proteins were found to lack the carboxyl terminus of STE18, including the CAAX box (Whiteway et al. supra).

An alignment of yeast Gγ, STE18, and mammalian Gγs can be made as indicated for the other G protein subunits. Such an alignment can be used in constructing mutant Gγ subunits or chimeric Gγ subunits. In preferred embodiments, mammalian Gγ2 is used in making G protein γ subunit chimeras.

VIII. Leader Sequences

It has been demonstrated that most of the mammalian extracellular, secreted proteins are poorly secreted when expressed in yeast. However, in many cases their secretion levels are markedly increased when their native signal sequences are replaced by the signal sequences of yeast proteins that interact more efficiently with the ER translocation complex. Specifically, the signal sequences of yeast invertase and acid phosphatase have been widely used in biotechnology to direct the secretory expression of the heterologous proteins. However, it is well established that even though many foreign proteins are targeted to the ER by the yeast signal sequences, not all of them advance further in the secretory pathway. The major problem appears to be in the malfolding and/or improper glycosylation of the heterologous proteins that results in their retention in the ER by the quality control apparatus of the yeast cell.

In many cases, the leader sequence of a precursor of yeast mating pheromone, α-factor, has been used successfully to overcome this problem (Brake, A. J. (1989) in *Yeast Genetic Engineering* (Barr, P. J., Brake, A. J., and Valenzuela, P., eds) pp. 269–280, Butterworths, London; Brake, A. J. (1990) *Meth. Enzymol.* 185, 408–441., and references cited therein). This sequence, in addition to the N-terminal signal peptide of 17 residues, includes a hydrophilic pro-region which contains 72 residues and bears three sites of N-linked glycosylation. The pro-region is extensively glycosylated in the ER and Golgi and is cleaved by Kex2 endopeptidase in the late Golgi compartment. The presence of the pro-region at the N-terminus has been demonstrated to promote transport of heterologous proteins from the ER to the periplasm. It is likely that the pro-region can somehow facilitate correct protein folding. Alternatively, it may be recognized by the quality control apparatus as a properly folded structural unit thus allowing an entire fusion protein to leave the ER.

The invertase leader can also be used. This leader sequence has been demonstrated to be cleaved from nascent invertase peptide, or nascent heterologous peptide, in the course of translocation into the endoplasmic reticulum.

A. Peptide Expression

In certain embodiments, such a leader sequence can be used to express a peptide library of the present invention. Yeast cells are bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides may either undergo re-uptake into the cell, transit through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the α-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion of peptides, or, if such secretion is provided, any particular secretion signal or transport pathway. In certain embodiments, peptides expressed with a signal sequence may bind to and activate receptors prior to their transport to the cell surface.

B. Receptor Expression

In other embodiments, a leader sequence of a yeast secreted protein can be used to direct transport of heterologous receptors to the plasma membrane. Previous work has demonstrated the expression of foreign, secreted proteins in yeast cells using the α-factor leader. However, when a heterologous membrane bound receptor, the rat M5 receptor, was expressed using such a system, it was found that the heterologous GPCR did not functionally integrate into the yeast cell signaling pathway (Huang et al. *Biochem. and Biophys. Res. Comm.* 1992. 182:1180). The transport of both secreted and transmembrane proteins into the endoplasmic reticulum in yeast is promoted by the same protein translocation complex, including the Sec61, Sec62 and Sec63 proteins. All the secreted proteins possess a signal sequence at their N-termini which is recognized by the translocation complex and serves as an ER targeting signal. A typical signal sequence is comprised of several positively charged residues at the N-terminus followed by a hydrophobic core and a C-terminal site of processing by signal peptidase. Some transmembrane proteins, for example, metabotropic glutamate receptors and vasoactive intestinal polypeptide receptors, also possess the N-terminal signal sequences, whereas some do not. In the latter case, a first transmembrane domain is believed to interact with the ER translocation machinery. The use of the α-factor leader sequence may, therefore, be particularly desirable for functional expression of certain receptors.

In certain embodiments, it will be desirable to further modify the yeast cells of the present invention. For example, in one embodiment it will be desirable to disrupt the yeast calnexin-like gene, CNE1, to improve receptor transport from the endoplasmic reticulum to the Golgi. In yet other embodiments, it will be desirable to overexpress the gene encoding Ast1, to increase transport form the Golgi to the plasma membrane. In yet other embodiments, it will be desirable to disrupt END3 and/or END4, to inhibit or prevent receptor internalization. Additionally or alternatively, the CHC1 gene (clathrin-encoding) can be disrupted to inhibit or prevent receptor internalization. In another embodiment, it may be desirable to disrupt the MVP-1 gene to inhibit or prevent transport from the Golgi to the pre-vacuolar compartment.

IX. Test Compounds

Exogenously Added Compounds

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. J. Am. Chem. Soc. 114:10987; DeWitt et al. 1993. Proc. Natl. Acad. Sci. USA 90:6909) peptoids (Zuckermann. 1994. J. Med. Chem. 37:2678) oligocarbamates (Cho et al. 1993. Science. 261: 1303), and hydantoins (DeWitt et al. supra). Rebek et al. have described an approach for the synthesis of molecular libraries of small organic molecules with a diversity of 104–105 (Carell et al. 1994. Angew. Chem. Int. Ed. Engl. 33:2059; Carell et al. Angew. Chem. Int. Ed. Engl. 1994. 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. Anticancer Drug Des. 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. Proc. Natl. Acad. Sci. USA 91:11422; Horwell et al. 1996 Immunopharmacology 33:68; and in Gallop et al. 1994. J. Med. Chem. 37:1233. In addition, libraries such as those described in the commonly owned applications U.S. Ser. No. 08/864,241, U.S. Ser. No. 08/864,240 and U.S. Ser. No. 08/835,623 can be used to provide compounds for testing in the present invention. The contents of each of these applications is expressly incorporated herein by this reference.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223, 409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

In certain embodiments, the test compounds are exogenously added to the host cells expressing a recombinant receptor and compounds that modulate signal transduction via the receptor are selected. In other embodiments, the host cells express the compounds to be tested. For example, a culture of the subject host cells can be further modified to collectively express a peptide library as described in more detail in PCT Publication WO 94/23025 the contents of which is expressly incorporated herein by this reference.

Other types of peptide libraries may also be expressed, see, for example, U.S. Pat. Nos. 5,270,181 and 5,292,646; and PCT publication WO94/02502). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

Autocrine Host Cells

In certain embodiments, host cells, e.g., can be engineered to produce the compounds to be tested. This assay system has the advantage of increasing the effective concentration of the compound to be tested. In one embodiment, a method such as that described in WO 94/23025 can be utilized.

Other methods can also be used. For example, peptide libraries are systems which simultaneously display, in a form which permits interaction with a target, a highly diverse and numerous collection of peptides. These peptides may be presented in solution (Houghten (1992) Biotechniques 13:412–421), or on beads (Lam (1991) Nature 354:82–84), chips (Fodor (1993) Nature 364:555–556), bacteria (Ladner U.S. Pat. No. 5,223,409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.). Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

The Ladner et al. patent, U.S. Ser. No. 5,096,815, describes a method of identifying novel proteins or polypeptides with a desired DNA binding activity. Semi-random ("variegated") DNA encoding a large number of different potential binding proteins is introduced, in expressible form, into suitable yeast cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., *J. Biol. Chem.* (1989) 264, 20206 and Kaiser et al. (1987) *Science* 235:312, respectively).

In certain embodiments of the instant invention, the compounds tested are in the form of peptides from a peptide library. The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO94/02502). The combinatorial peptide can be attached on the terminus of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is a combinatorial library of polypeptides which are based at least in part on a known polypeptide sequence or a portion thereof (not a cDNA library). That is, the sequences of the library is semi-random, being derived by combinatorial mutagenesis of a known sequence. See, for example, Ladner et al. PCT publication WO 90/02909; Garrard et al., PCT publication WO 92/09690; Marks et al. (1992) *J. Biol. Chem.* 267: 16007–16010; Griffths et al. (1993) *EMBO J* 12:725–734; Clackson et al. (1991) *Nature* 352:624–628; and Barbas et al. (1992) *PNAS* 89:4457–4461. Accordingly, polypeptide(s) which are known ligands for a target receptor can be mutagenized by standard techniques to derive a variegated library of polypeptide sequences which can further be screened for agonists and/or antagonists. For example, DNA encoding a surrogate ligand can be mutagenized to generate a library encoding peptides with some relationship to the original peptide. This library can be expressed in a reagent cell of the present invention, and other receptor activators can be isolated from the library. This may permit the identification of even more potent surrogate ligands.

In still another embodiment, the combinatorial polypeptides are produced from a cDNA library.

In a preferred embodiment of the present invention, the host cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In certain embodiments of the present invention, the peptides of the library are encoded by a mixture of DNA molecules of different sequence. Each peptide-encoding DNA molecule is ligated with a vector DNA molecule and the resulting recombinant DNA molecule is introduced into a host cell. Since it is a matter of chance which peptide-encoding DNA molecule is introduced into a particular cell, it is not predictable which peptide that cell will produce. However, based on a knowledge of the manner in which the mixture was prepared, one may make certain statistical predictions about the mixture of peptides in the peptide library.

The peptides of the library can be composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

X. Screening and Selection: Assays of Second Messenger Generation

When screening for bioactivity of compounds, intracellular second messenger generation can be measured directly. A variety of intracellular effectors have been identified as being G-protein-regulated, including adenylyl cyclase, cyclic GMP, phosphodiesterases, phosphoinositidase C, and phospholipase $A_2$. In addition, G proteins interact with a range of ion channels and are able to inhibit certain voltage-sensitive $Ca^{++}$ transients, as well as stimulating cardiac $K^+$ channels.

In one embodiment, the GTPase enzymatic activity by G proteins can be measured in plasma membrane preparations by determining the breakdown of $\gamma^{32}P$ GTP using techniques that are known in the art (For example, see *Signal Transduction: A Practical Approach*. G. Milligan, Ed. Oxford University Press, Oxford England). When receptors that modulate cAMP are tested, it will be possible to use standard techniques for cAMP detection, such as competitive assays which quantitate [$^3$H]cAMP in the presence of unlabelled cAMP.

Certain receptors stimulate the activity of phospholipase C which stimulates the breakdown of phosphatidylinositol 4,5, bisphosphate to 1,4,5-IP3 (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) *Environ Health Perspect* 84:45–56). As an exemplary method of Ca++ detection, cells could be loaded with the Ca++ sensitive fluorescent dye fura-2 or indo-1, using standard methods, and any change in Ca++ measured using a fluorometer.

The other product of PIP2 breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In the case of certain receptors, it may be desirable to screen for changes in cellular phosphorylation. Such assay formats may be useful when the receptor of interest is a receptor tyrosine kinase. For example, yeast transformed with the FGF receptor and a ligand which binds the FGF receptor could be screened using colony immunoblotting (Lyons and Nelson (1984) *Proc. Natl. Acad. Sci. USA* 81:7426–7430) using anti-phosphotyrosine. In addition, tests for phosphorylation could be useful when a receptor which may not itself be a tyrosine kinase, activates protein kinases that function downstream in the signal transduction pathway. Likewise, it is noted that protein phosphorylation also plays a critical role in cascades that serve to amplify signals generated at the receptor. Multi-kinase cascades allow not only signal amplification but also signal divergence to multiple effectors that are often cell-type specific, allowing a growth factor to stimulate mitosis of one cell and differentiation of another.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the *S. cerevisiae* pheromone signaling pathway is comprised of a protein kinase cascade composed of the products of the STE11, STE7, and FUS3/KSS1 genes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

Modified methods for detecting receptor-mediated signal transduction exist and one of skill in the art will recognize suitable methods that may be used to substitute for the example methods listed.

In one embodiment, the indicator gene can be used for detection. In one embodiment an indicator gene is an unmodified endogenous gene. For example, the instant method can rely on detecting the transcriptional level of such pheromone response pathway responsive endogenous genes as the Bar1 or Fus1, Fus 2, mating factor, Ste3 Ste13, Kex1, Ste2, Ste6, Ste7, Sst2, or Chs1. (Appletauer and Zchstetter. 1989. Eur. J. Biochem. 181:243)

In other embodiments, the sensitivity of an endogenous indicator gene can be enhanced by manipulating the promoter sequence at the natural locus for the indicator gene. Such manipulation may range from point mutations to the endogenous regulatory elements to gross replacement of all or substantial portions of the regulatory elements. The previous discussion of mutations with regard to G proteins and G protein-coupled receptors is reiterated here.

For example, in the case of the Bar1 gene, the promoter of the gene can be modified to enhance the transcription of Bar1 upon activation of the yeast pheromone response pathway. Bar1 gene transcription is inactivated upon exposure of yeast cells to mating factor. The sequence of the Bar1 gene is known in the art (see e.g., U.S. Pat. No. 4,613,572). Moreover, the sequences required for a-factor-enhanced expression of the Bar1, and other pheromone responsive genes have been identified. (Appeltauer and Achstetter 1989. Eur. J. Biochem. 181:243; Hagen et al. 1991. Mol. Cell. Biol. 11:2952). In an exemplary embodiment, the yeast Bar1 promoter can be engineered by mutagenesis to be more responsive, e.g., to more strongly promoter gene transcription, upon stimulation of the yeast pheromone pathway. Standard techniques for mutagenizing the promoter can be used. In such embodiments, it is desirable that the conserved oligonucleotide motif described by Appeltaure et al. be conserved.

In yet other embodiments, rather than measuring second messenger production or alterations in transcription, the activity of endogenous yeast proteins can be assayed. For example, in one embodiment, the signal transduction pathway of the receptor upregulates expression or otherwise activates an enzyme which is capable of modifying a substrate which can be added to the cell. The signal can be detected by using a detectable substrate, in which case loss of the substrate signal is monitored, or alternatively, by using a substrate which produces a detectable product. In certain embodiments, the substrate is naturally occurring. Alternatively, the substrate can be non-naturally occurring. In preferred embodiments, BAR1 activity can be measured.

In other embodiments, the modulation of a receptor by a test compound can result in a change in the transcription of a gene, which is not normally pheromone responsive. In preferred embodiments, the gene is easily detectable. For example, in a preferred embodiment, the subject assay can be used to measure Pho5, a secreted acid phosphatase. Acid phosphatase activity can be measured using standard techniques.

In other embodiments, reporter gene constructs can be used. Reporter gene constructs are prepared by operatively linking a reporter gene with at least one transcriptional regulatory element. If only one transcriptional regulatory element is included it must be a regulatable promoter. At least one of the selected transcriptional regulatory elements must be indirectly or directly regulated by the activity of the selected cell-surface receptor whereby activity of the receptor can be monitored via transcription of the reporter genes.

Many reporter genes and transcriptional regulatory elements are known to those of skill in the art and others may be identified or synthesized by methods known to those of skill in the art. Reporter genes include any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101); human placental secreted alkaline phosphatase (Cullen and Malim (1992) Methods in Enzymol. 216:362–368) and green fluorescent protein (U.S. Pat. No. 5,491,084; WO96/23898).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Other promoters and transcriptional control elements, in addition to those described above, include the vasoactive intestinal peptide (VIP) gene promoter (cAMP responsive; Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP, nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum; Changelian et al. (1989). Proc. Natl. Acad. Sci. 86:377–381); and others that may be known to or prepared by those of skill in the art.

In certain assays it may be desirable to use changes in growth in the screening procedure. For example, one of the consequences of activation of the pheromone signal pathway in wild-type yeast is growth arrest. If one is testing for an antagonist of a G protein-coupled receptor, this normal response of growth arrest can be used to select cells in which the pheromone response pathway is inhibited. That is, cells exposed to both a known agonist and a peptide of unknown activity will be growth arrested if the peptide is neutral or an agonist, but will grow normally if the peptide is an antagonist. Thus, the growth arrest response can be used to advantage to discover peptides that function as antagonists.

In certain embodiments, when searching for compounds which can function as agonists of G protein-coupled receptors, or other pheromone system proteins, the growth arrest consequent to activation of the pheromone response pathway is an undesirable effect since cells that bind agonists stop growing while surrounding cells that fail to bind agonists will continue to grow. The cells of interest, then, will be overgrown or their detection obscured by the background cells, confounding identification of the cells of interest. To overcome this problem the present invention teaches engineering the cell such that: 1) growth arrest does not occur as a result of exogenous signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter, and applying selective conditions).

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA-binding repressor protein, and incorporating a suitable operator site into the promoter or other suitable region of the marker gene.

In the case of yeast, exemplary positively selectable (beneficial) genes include the following: URA3, LYS2, HIS3, LEU2, TRP1; ADE1,2,3,4,5,7,8, ARG1, 3, 4, 5, 6, 8; HIS1, 4, 5; ILV1, 2, 5; THR1, 4; TRP2, 3, 4, 5; LEU1, 4; MET2,3,4,8,9,14,16,19; URA1,2,4,5,10; HOM3,6; ASP3; CHO1; ARO 2,7; CYS3, OLE1; INO1,2,4; PRO1,3 Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In another version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase; inhibits growth on α-aminoadipate as sole nitrogen source), CYH2 (encodes ribosomal protein L29; cycloheximide-sensitive allele is dominant to resistant allele), CAN1 (encodes arginine permease; null allele confers resistance to the arginine analog canavanine), and other recessive drug-resistant markers.

In one example, the reporter gene effects yeast cell growth. The natural response to signal transduction via the yeast pheromone system response pathway is for cells to undergo growth arrest. This is a preferred way to select for antagonists of a ligand/receptor pair that stimulates a the pathway. An antagonist would inhibit the activation of the pathway; hence, the cell would be able to grow. Thus, the FAR1 gene may be considered an endogenous counterselectable marker. The FAR1 gene is preferably inactivated when screening for agonist activity.

The reporter gene may also be a screenable gene. The screened characteristic may be a change in cell morphology, metabolism or other screenable features. Suitable markers include beta-galactosidase (Xgal, $C_{12}FDG$, Salmon-gal, Magenta-Gal (latter two from Biosynth Ag)), alkaline phosphatase, horseradish peroxidase, exo-glucanase (product of yeast exbl gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment. Again, the promoter may be receptor-induced or receptor-inhibited.

XI. Other Optional Alterations to Yeast Cells

The choice of appropriate host cell will also be influenced by the choice of detection signal. For instance, reporter constructs can provide a selectable or screenable trait upon transcriptional activation (or inactivation) in response to a signal transduction pathway coupled to the target receptor. The indicator gene may be an unmodified gene already in the host cell pathway, such as the genes responsible for growth arrest in yeast. In certain embodiments a host cell gene may be operably linked to a "receptor-responsive" promoter. Alternatively, it may be a heterologous gene that has been so linked. Suitable genes and promoters are discussed below.

To achieve optimal selection or screening, the host cell phenotype will be considered. For example, introducing a pheromone-responsive chimeric HIS3 gene into a yeast that has a wild-type HIS3 gene would frustrate genetic selection. Thus, to achieve nutritional selection, an auxotrophic strain is preferred. Yeast strains that are auxotrophic for histidine (HIS3) are known, see Struhl and Hill, (1987) *Mol. Cell. Biol.*, 7:104; Fasullo and Davis, *Mol. Cell. Biol.*, (1988) 8:4370. The HIS3 (imidazoleglycerol phosphate dehydratase) gene has been used as a selective marker in yeast. See Sikorski and Heiter, (1989) Genetics, 122:19; Struhl, et al., P.N.A.S. (1979) 76:1035; and, for FUS1-HIS3 fusions, see Stevenson, et al., (1992) *Genes Dev.*, 6:1293.

In certain embodiments, the host cell can be modified in other ways. For example, when the host cell is a yeast cell it may be desirable to inactivate, such as by mutation or deletion, a homologous receptor, e.g., a pheromone receptor, present in the cell in order to minimize interference with signaling via the heterologous receptor. "Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

In a preferred embodiment of the subject assay, the yeast cells possess one or more of the following characteristics: (a) the endogenous FUS1 gene has been inactivated; (b) the endogenous SST2 gene, and/or other genes involved in desensitization, have been inactivated; (c) if there is a homologous, endogenous receptor gene it has been inactivated; and (d) if the yeast produces an endogenous ligand to the exogenous receptor, the genes encoding for the ligand been inactivated.

It is desirable that the exogenous receptor be exposed on a continuing basis to the peptides. In some instances, this may result in desensitization of the pheromone pathway to the stimulus. For example, the mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, J. B. (1993) *Mol. Cell. Biol.* 13:6876–6888) and SGV1, MSG5, and SIGI genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations e.g. STE50, sgv1, bar1, ste2, ste3, pik1, msg5, sig1, and aft1, have the similar effect of increasing the sensitivity of the bioassay. Thus desensitization may be avoided by mutating (which may include deleting) the SST2 gene so that it no longer produces a functional protein, or by mutating one of the other genes listed above.

In certain embodiments, it will be desirable to complement the host yeast cells, e.g., at least partial function of an inactivated gene of the host cell can be supplied by an exogenous nucleic acid. For instance, yeast cells can be "mammalianized", and even "humanized", by complementation of receptor and signal transduction proteins with mammalian homologues. To illustrate, inactivation of a yeast Byr2/Ste11 gene can be complemented by expression of a human MEKK gene.

Complementations for use in the subject assay can be constructed without any undue experimentation. Indeed, many yeast genetic complementations with mammalian signal transduction proteins have been described in the art. For example, Mosteller et al. (1994) Mol Cell Biol 14:1104–12 demonstrates that human Ras proteins can complement loss of ras mutations in *S. cerevisiae*. Moreover, Toda et al. (1986) Princess Takamatsu Symp 17: 253–60 have shown that human ras proteins can complement the loss of RAS 1 and RAS2 proteins in yeast, and hence are functionally homologous. Both human and yeast RAS proteins can stimulate the magnesium and guanine nucleotide-dependent adenylate cyclase activity present in yeast membranes. Ballester et al. (1989) Cell 59: 681–6 describe a vector to express the mammalian GAP protein in the yeast *S. cerevisiae*. When expressed in yeast, GAP inhibits the function of the human ras protein, and complements the loss of IRA1. IRA1 is a yeast gene that encodes a protein with homology to GAP and acts upstream of RAS. Mammalian GAP can therefore function in yeast and interact with yeast RAS. Wei et al. (1994) Gene 151: 279–84 describes that a human Ras-specific guanine nucleotide-exchange factor, Cdc25GEF, can complement the loss of CDC25 function in *S. cerevisiae*. Martegani et al. (1992) EMBO J 11: 2151–7 describe the cloning by functional complementation of a mouse cDNA encoding a homolog of CDC25, a *Saccharomyces cerevisiae* RAS activator. Vojtek et al. (1993) J Cell Sci 105: 777–85 and Matviw et al. (1992) Mol Cell Biol 12: 5033–40 describe how a mouse CAP protein, e.g., an adenylyl cyclase associated protein associated with ras-mediated signal transduction, can complements defects in *S. cerevisiae*. Papasavvas et al. (1992) Biochem Biophys Res Commun 184:1378–85 also suggest that inactivated yeast adenyl cyclase can be complemented by a mammalian adenyl cyclase gene. Hughes et al. (1993) Nature 364: 349–52 describe the complementation of byr1 in fission yeast by mammalian MAP kinase kinase (MEK). Parissenti et al. (1993) Mol Cell Endocrinol 98: 9–16 describes the reconstitution of bovine protein kinase C (PKC) in yeast. The Ca(2$^+$) and phospholipid-dependent Ser/Thr kinase PKC plays important roles in the transduction of cellular signals in mammalian cells. Marcus et al. (1995) *PNAS* 92: 6180–4 suggests the complementation of shk1 null mutations in *S. pombe* by the either the structurally related *S. cerevisiae* Ste20 or mammalian p65PAK protein kinases.

XII. Pharmaceutical Preparations of Identified Compounds

After identifying certain test compounds as potential surrogate ligands, or receptor antagonists, the practitioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The compounds selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

All patents, published patent applications and other references disclosed herein are hereby expressly incorporated by reference. In addition the contents of U.S. Ser. Nos. 08/322,137; 08/463,181; 08/655,192; 08/689,172; 08/936,632 and 08/946,298 are hereby incorporated by this reference.

EXEMPLIFICATION

The invention now being generally described will be more readily understood by reference to the following examples, which are included merely for purposes of illustration of certain aspects and embodiments of the present invention and are not intended to limit the invention.

EXAMPLE 1

Expression of the IL-8A Receptor in Cells

The IL-8A receptor was expressed in both yeast and mammalian cells. For expression of the IL-8A receptor, an expression plasmid was derived from p1289, which contains the LEU2 gene as a selectable marker and directs constitutive expression from the PGK promoter. The rabbit IL8A receptor was cloned from rabbit genomic DNA using the oligonucleotides "IL8R1FWD" (5'-CCCCCATGG AAG-TAAACGTATGGAATATG-3') (SEQ ID NO: 11) and "IL8R1REV" (5'-CCCTCTAGAGATTTGA AGGCACGT-TGG-3') (SEQ ID NO: 12). Cp2687 was constructed by subcloning the PCR product into p1289 using NcoI and XbaI as 5' and 3' cloning sites. As the rabbit IL8AR gene contains an internal NcoI site, the receptor was, in fact, cloned as two pieces rejoined.

The yeast strain CY1141 (MATa far1D1442 tbt1-1 fus1-HIS3 can1ste14::trp1::LYS2 ste3D1156gpa1(41)-Gai2 lys2 ura3 leu2 trp1 his3) was constructed using standard genetic techniques and used for IL-8 receptor expression. The rabbit IL8A receptor couples to the pheromone response pathway in yeast through the Gpa1-Gαi2 chimera.

For mammalian cell expression of the IL-8A receptor, HEK293 cells were used. HEK 293 cells stably expressing Gα16 were maintained in DMEM supplemented with 10% New Calf Serum and 200(g/ml G418). Cells at ~70% confluence were transfected with plasmids encoding the WT or mutant (made as described below) rabbit IL8A receptors and stable transfectants were selected in the presence of 400 mg/ml hygromycin. Cells were maintained in selection medium for 7–9 days until the surviving cells expanded to 80–90% confluence.

EXAMPLE 2

Expression of Ligands of the IL-8 Receptor

There are two known human subtypes of the IL8 receptor. Subtype A (CXCR1) binds IL8 with high affinity ($K_d$=0.1–1 nM) but shows very low affinity binding to GROα and NAP-2 ($K_d$>100 nM). Subtype B (CXCR2) binds all three ligands with high affinity.

Cells were constructed which coexpressed the IL-8 receptor and IL-8A receptor ligands. For ligand expression, plasmids were derived from the plasmid p1624 containing the URA3 gene as a selectable marker and the ADH1 promoter directing the constitutive expression of an Mfa signal sequence and leader. The ligand ORF was cloned into this plasmid using an AflII site at the 5'end and a BglII site at the 3' end to create a fusion junction of the indicated structure:

```
IL-8    LKR   SAKELRCQCI...    (SEQ ID NO:13)

MGSA    LKR   ASVATELRCQCL...  (SEQ ID NO:14)

NAP2    LKR       AELRCMCI..   (SEQ ID NO:15)
```

The ligand genes were assembled by annealing the oligonucleotides described below with their complementary oligonucleotide, followed by ligation together into Cp1624 digested with AflII and BglII.

IL-8 (to yield the plasmid Cp1358):

```
IL8-1  TTAAGCGTGAGGCAGAAGCTTCTGCTAAGGAATTGAGATGTCAATGTATTAAGACTT        (SEQ ID NO:16)

1L8-2  ACTCTAAGCCATTCCATCCAAAGTTCATTAAGGAATTGAGAGTTATTGAATCTGGTCCA      (SEQ ID NO:17)

IL8-3  CATTGTGCTAACACTGAAATTATTGTTAAGTTGTCTGATGGTAGAGAATTGTGTTTGGAT     (SEQ ID NO:18)

IL8-4  CCAAAGGAAAACTGGGTTCAAAGAGTTGTTGAAAAGTTCTTGAAGAGAGCTGAAAACTCTTGA  (SEQ ID NO:19)

1L8-5  TAGAGTAAGTCTTAATACATTGACATCTCAATTCCTTAGCAGAAGCTTCTGCCTCACGC      (SEQ ID NO:20)

IL8-6  ACAATGTGGACCAGATTCAATAACTCTCAATTCCTTAATGAACTTTGGATGGAATGGCT      (SEQ ID NO:21)

IL8-7  CTTTGGATCCAAACACAATTCTCTACCATCAGACAACTTAACAATAATTTCAGTGTTAGC    (SEQ ID NO:22)

IL8-8  GATCTCAAGAGTTTTCAGCTCTCTTCAAGAACTTTTCAACAACTCTTTGAACCCAGTTTTC   (SEQ ID NO:23)
```

The IL8 coding sequenced was subsequently amplified from Cp1358 using af12-72-i18 (CCGCTTAAGCGTTCT-GCTAAGGAATTGAGATGTC) (SEQ ID NO:24) and PX25 (AAGTATATTGTATTTTGTACGAGC) (SEQ ID NO:25), digested with AflII and BglII, and reintroduced into Cp1624 to create the junction indicated above.

MGSA/GROα (to yield the plasmid Cp2685):

```
MGOPTF1  TTAAGCGTGCGTCCGTTGCTACAGAATTGAGGTGTCAATGTCTACAAACTTTGCAA         (SEQ ID NO:26)

MGOPTF2  GGTATCCACCCAAAGAACATTCAGTCAGTCAGTTAACGTTAAGTCCCCAGGTCCACACTGTGC  (SEQ ID NO:27)

MGOPTF3  TCAGACTGAAGTCATAGCTACATTAAAGAATGGTCGTAAAGCCTGTTTAAATCCTGC        (SEQ ID NO:28)

MGOPTF4  ATCCCCAATAGTAAAGAAAATCATCGAAAAGATGTTGAATAGTGATAAATCCAATTAA       (SEQ ID NO:29)

MGOPTR1  GATCTTAATTGGATTTATCACTATTCAACATCTTTTCGATGATTTTCTTTACTATTGG       (SEQ ID NO:30)

MGOPTR2  GGATGCAGGATTTAAACAGGCTTTACGACCATTCTTTAATGTAGCTATGACTTCAGT        (SEQ ID NO:31)
```

-continued

```
MGOPTR3  CTGAGCACAGTGTGGACCTGGGGACTTAACGTTAACTGACTGAATGTTCTTTGGGTGGA    (SEQ ID NO:32)

MGOPTR4  TACCTTGCAAAGTTTGTAGACATTGACACCTCAATTCTGTAGCAACGGACGCACGC       (SEQ ID NO:33)
```

CY9158 is the CY1141 strain harboring the plasmid (Cp2685) that expresses human GROα. To achieve expression of secreted human GROα, the coding sequence of GROα was fused to sequences encoding the signal and leader sequences of the yeast MFa1 gene, and placed this fusion protein under the control of the constitutive ADH1 promoter.

NAP2 (to yield the plasmid Cp2674):

```
NAP2F1  TTAAGCGTGCTGAATTGAGATGTATGTGTATCAAGACCACCTCTGGTATCCACCC     (SEQ ID NO:34)

NAP2F2  AAAGAACATCCAATCTTTGGAAGTTATCGGTAAGGGTACTCACTGTAACCAAGTT     (SEQ ID NO:35)

NAP2F3  GAAGTTATCGCTACCTTGAAGGACGGTAGAAAGATTTGTTTGGACCCAGACGCTC     (SEQ ID NO:36)

NAP2F4  CAAGAATCAAGAAGATCGTTCAAAAGAAGTTGGCTGGTGACGAATCTGCTGACTA     (SEQ ID NO:37)

NAP2R1  GATCTAGTCAGCAGATTCGTCACCAGCCAACTTCTTTTGAACGATCTTCTTGATT     (SEQ ID NO:38)

NAP2R2  CTTGGAGCGTCTGGGTCCAAACAAATCTTTCTACCGTCCTTCAAGGTAGCGATAA     (SEQ ID NO:39)

NAP2R3  CTTCAACTTGGTTACAGTGAGTACCCTTACCGATAACTTCCAAAGATTGGATGTT     (SEQ ID NO:40)

NAP2R4  CTTTGGGTGGATACCAGAGGTGGTCTTGATACACATACATCTCAATTCAGCACGC     (SEQ ID NO:41)
```

EXAMPLE 2

Creation of IL-8A Receptor Mutants

By random mutagenesis of the JL-8 receptor, mutants that show altered coupling behavior to the ligands GROα and NAP-2, as well as showing an enhanced response to IL8 have been isolated.

The plasmid Cp2687, encoding the gene for the rabbit JL8A receptor under the control of the constitutive PGK1 promoter, was randomly mutagenized using hydroxylamine and introduced into CY9158 (which expresses human GROα). Hydroxyl amine mutagenesis was performed by incubating 10 mg Cp2687 (containing the IL-8A receptor) in 500 ml of 7% HONH$_2$.HCl. 1.8% NaOH for 24 hours at 37°. The DNA was ethanol precipitated, resuspended in ddH$_2$O and introduced into CY9158 using lithium acetate.

Approximately 30,000 yeast colonies were selected on SCLU (SCLU contains a mixture of amino acids lacking leucine and uracil; the pH was adjusted to 6.8 using 4.5 ml 1M KOH and 25 ml 1M K-Pipes pH 6.8 per liter), and after 2 days of growth at 30° C., the colonies were replica plated to the same media lacking histidine and containing 1 mM 3-aminotriazole (AT, a competitive inhibitor of the His3 gene product) (SCHI media). Yeast cells expressing the wild-type receptor do not grow on this media since GROα activates this receptor poorly if at all; the fus1-HIS3 construct, which serves as a measure of pathway activation, is therefore repressed and the cells remain auxotrophic for histidine. Therefore, only cells expressing receptors that have gained the ability to be activated by GROα are selected on this media. Approximately 200 such colonies were identified. FIG. 1 shows the GROα and NAP-2 dependent growth of yeast strains expressing the mutant receptors, as well as the inability of these ligands to activate wild-type receptor.

Figure 2:
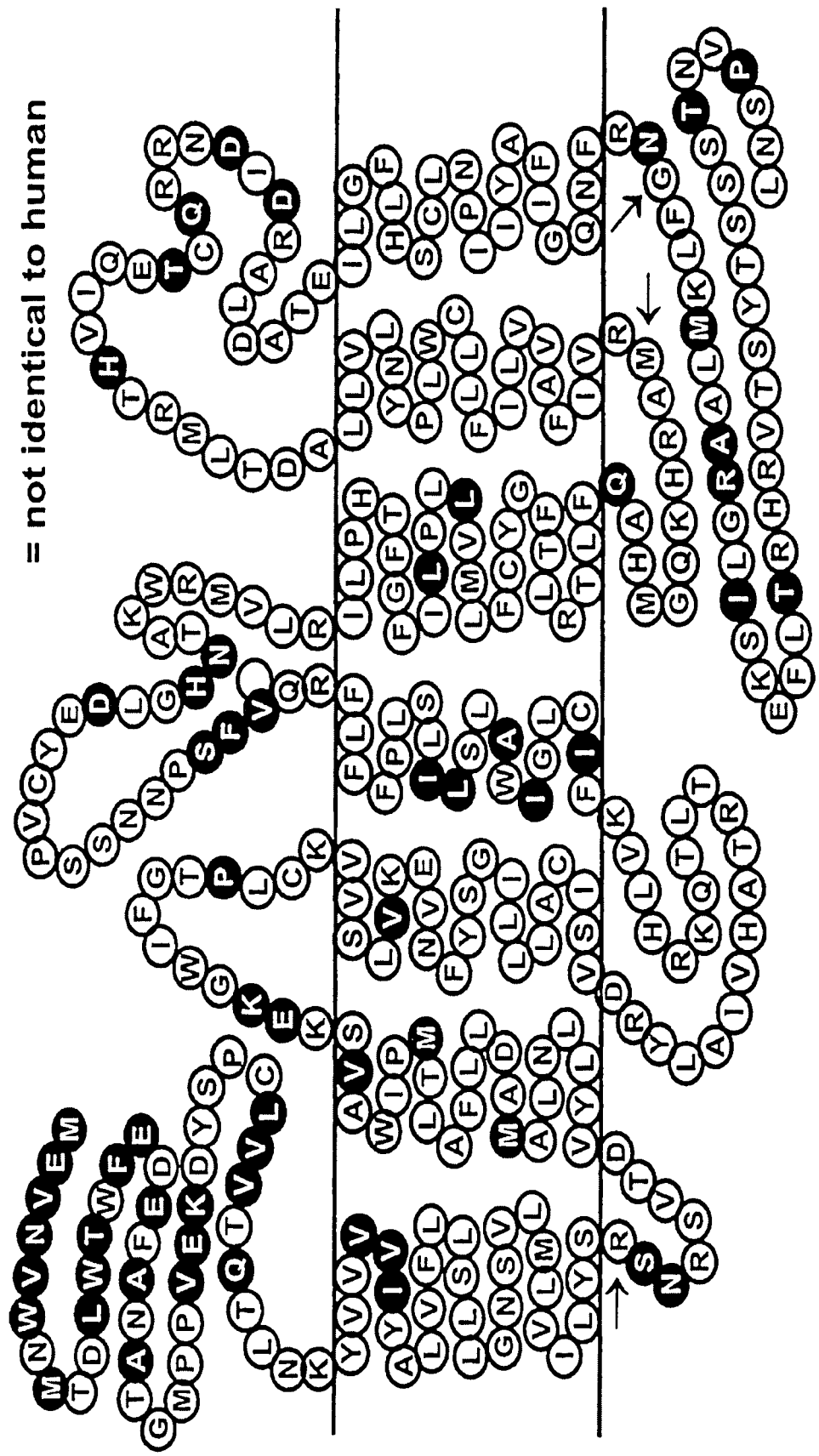
FIG. 2 shows amino acid sequence (SEQ ID NO: 48) of the rabbit IL8A receptor showing putative membrane spanning domains. Arg73 ($1^{st}$ intracellular loop), Met246 ($3^{rd}$ intracellular loop) and Gly320 (C-terminal tail) are indicated with arrows.

Sequencing of the receptor plasmids showed that all the mutations found were in the intracellular loops and the C-terminal tail (FIG. 2). Using single amino acid code, the mutations identified were:

R73W (i.e., at position 73 an Arginine to Tryptophan mutation)—(CGG to TGG)

M246I—(ATG to ATA)

G320R—(GGA to AGA)

Subsequent segregation of Cp2685 (URA3$^+$ PGKp-GROα) demonstrated that the His$^+$ phenotype was dependent on the presence of GROα. Ura$^-$ progeny selected by their ability to grow in the presence of 5-fluoro orotic acid were no longer able to grow on SCLH1. Plasmid DNA was recovered from colonies that showed GROα-dependent growth and reintroduced into CY9158 to ensure that the mutated DNA was able to confer the identical His$^+$ phenotype to a naive host.

Figure 3:
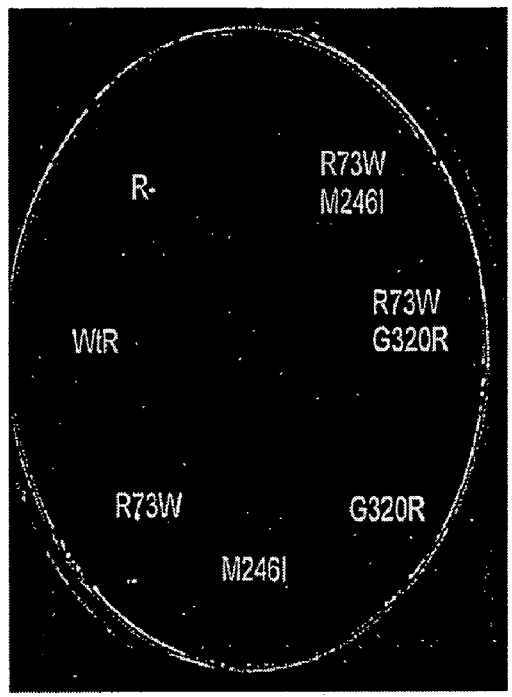
FIG. 3 shows enhanced growth phenotype of mutant receptors.
Figure 3:
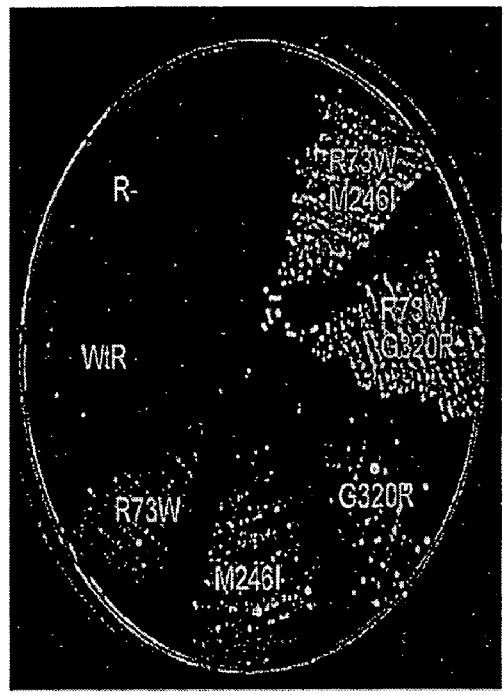
Figure 3:
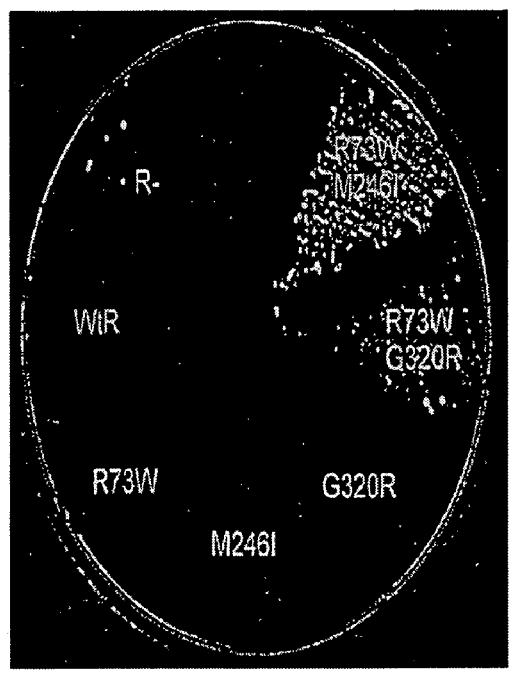
Figure 3:
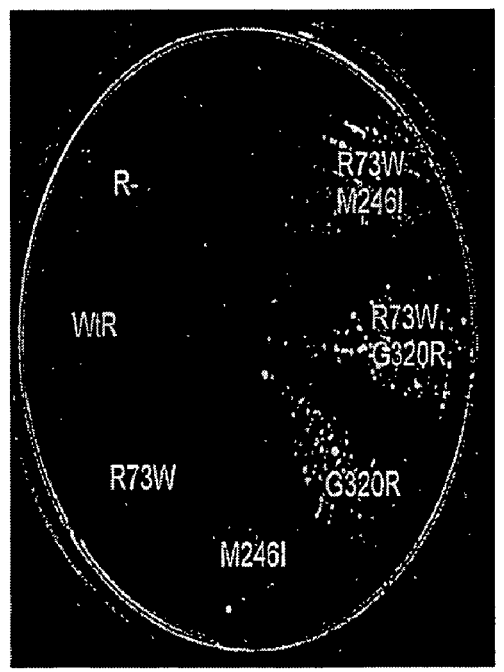
Figure 4:
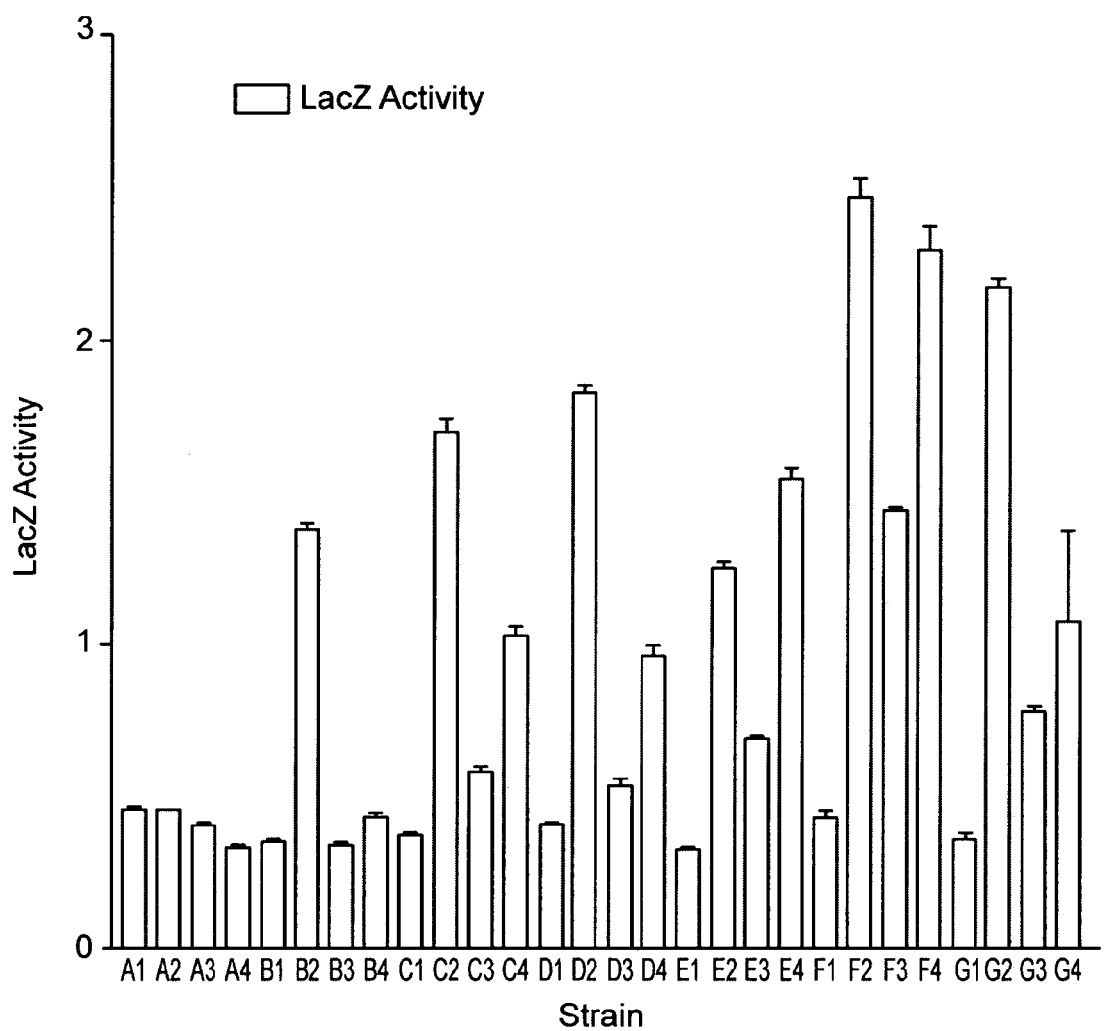
FIG. 4 shows FUS1-lacZ activity in autocrine strains expressing wild type or mutant receptors.

Plasmids expressing double mutants were constructed by replacing a BamHI/XbaI fragment from the R73W mutant with that from either the M246I or the G320R mutants. When these mutations are combined, the growth phenotype is enhanced. This is clear when their growth is compared on media containing 10 mM 3-AT, a concentration which demands higher expression of His3 to confer histidine prototrophy (FIG. 3).

β-galactosidase activity arising from the expression of a fus1-lacZ plasmid (Cp 1584) can be measured either in autocrine strains (expressing ligand endogenously) or in cells that are supplied with agonist exogenously. In autocrine strains, the response to IL-8 and NAP-2 is consistent with the results of the fus1-HIS3 assay, but the response of these mutants to GROα is greatly diminished (FIG. 4). The reason for this discrepancy may lie in the fact that the growth assay measures activation over a period of days, while the fus1-lacZ assay measures accumulation of enzyme over a period of a few hours. The b-galactosidase assays were performed using ONPG as substrate (Mol. Cell. Biol. 7:2316). For CPRG assays, 100 ml of cells in synthetic media were mixed with 20 ml of 1.6 mg/ml CPRG in 2.5% Triton X-100/138 mM K-Pipes pH 6.8, and incubated at 37° C. The reactions were stopped by the addition of 10 ml of 1M Na$_2$CO$_3$ and the absorbance was measured at 578 nm. Dose responses using IL8, GROα or NAP-2 (R&D Systems) were performed by incubating logarithmic cultures in SCLUT (SCLUT lacks leucine, uracil and tryptophan) with the indicated amount of agonist for the indicated times at 30° prior to the addition of the lysis/substrate buffer.

Figure 5:
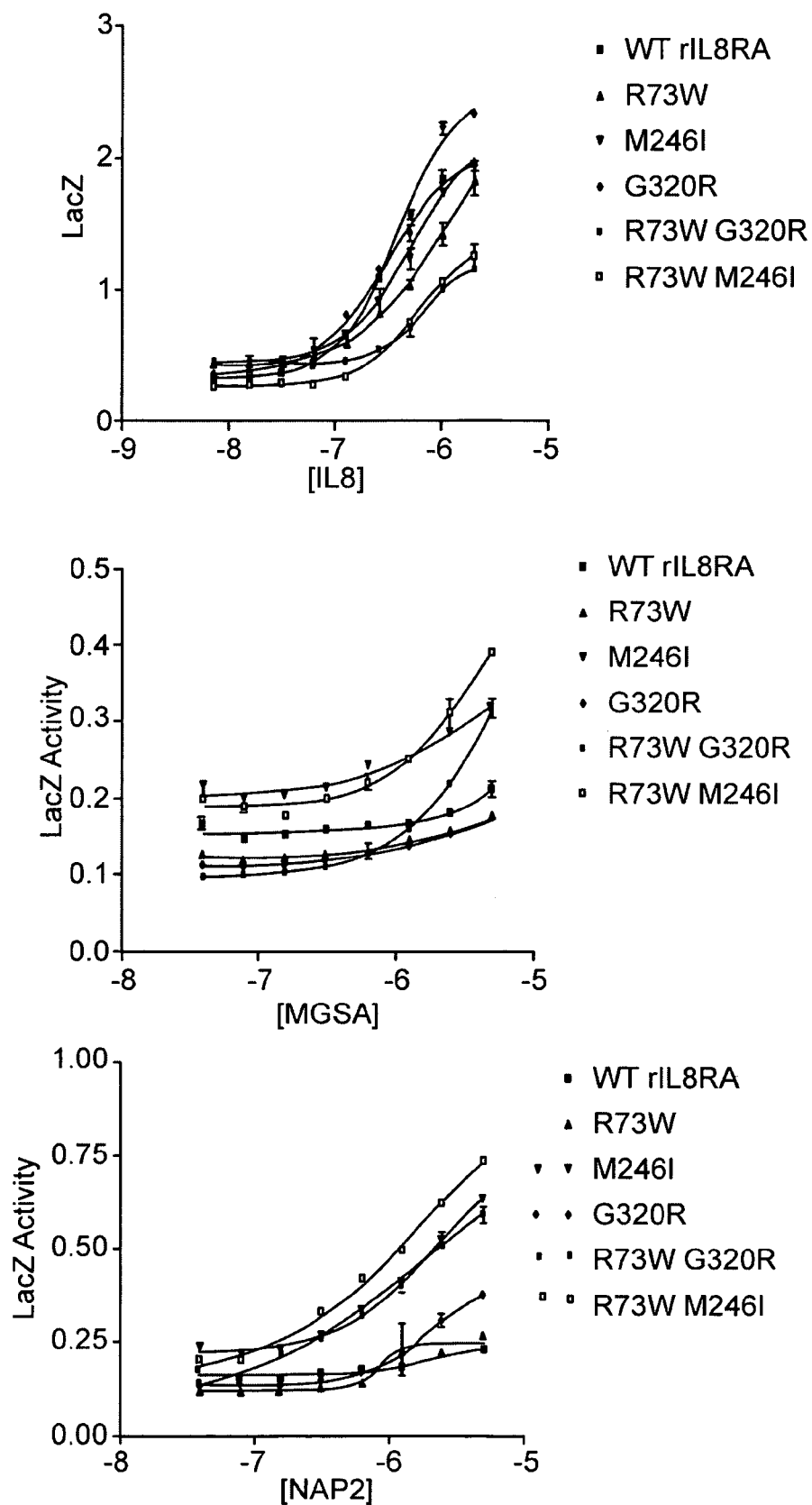
FIG. 5 shows activation of wild type or mutant IL8 receptors by exogenous IL8 (A), GROα (B) or NAP-2 (C).

The results of such assays with IL8, GROα or NAP-2 being provided exogenously are shown in FIG. 5. When ligand is applied exogenously, fus1-lacZ activity in yeast strains expressing the rabbit IL8AR increases in a dose dependent manner. The response of all the single mutants and at least one of the double mutants (R73W M246I) to IL8 is significantly increased with respect to wild type receptor (FIG. 25A). In the assay with NAP-2, both double mutants and the M246I mutant show enhanced coupling over the wild type receptor (FIG. 5C). $EC_{50}$ values could not be obtained since the assay was not saturated at the highest ligand concentration (5(M), an obstacle that is magnified in the GROα assay (FIG. 5B).

Figure 6:
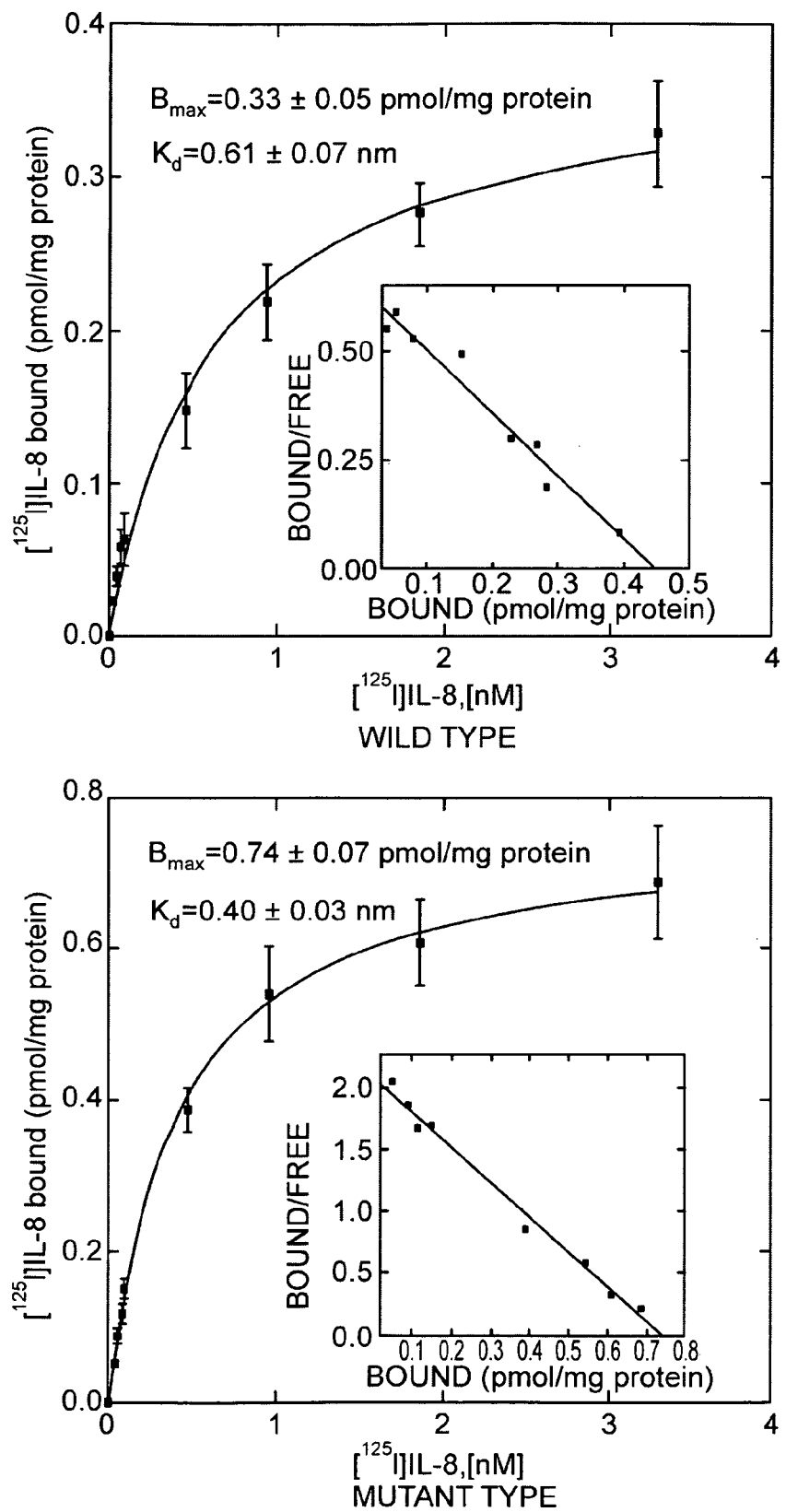
FIG. 6 shows saturation binding of [$^{125}$I] IL8 to membranes from yeast cells expressing the wild type IL8 receptor or the Arg73Trp Gly320Arg double mutant.

Ligand binding assays with membranes from yeast strains expressing the WT rIL8 receptor or the double mutant R73W G320R, showed a slight difference in binding affinity for either IL8 or GROα((FIG. 6), although the mutant showed a 2-fold increase in the $B_{max}$.

In order to study the effects of these mutations on receptor function in mammalian cells, the mutant receptors were cloned into a mammalian expression vector and transfected into HEK293/Ga16 cells, which stably express a Ga16 construct. $Ca^{++}$ fluxes in response to agonist were measured in a dose response assay and in a pertussis toxin experiment. To measure Ca++ flux, transfected cells were transferred to black-walled 96-well plates at $9 \times 10^6$ cells/well. After 24 hours of growth in the presence or absence of pertussis toxin (0.5 mg per ml; Calbiochem), the growth medium was removed and the cells were loaded with the fluorescent dye Fluo-3 for 1 hr at 37° in the presence of 20 mM Probenicid (Sigma). Each well was washed with Hanks buffered salt solution/20 mM HEPES/20 mM Probenicid. The appropriate amount of agonist was added and fluorescence intensity was measured over a period of 5 minutes using a Fluorescence Imaging Plate Reader (Molecular Devices).

Figure 8:
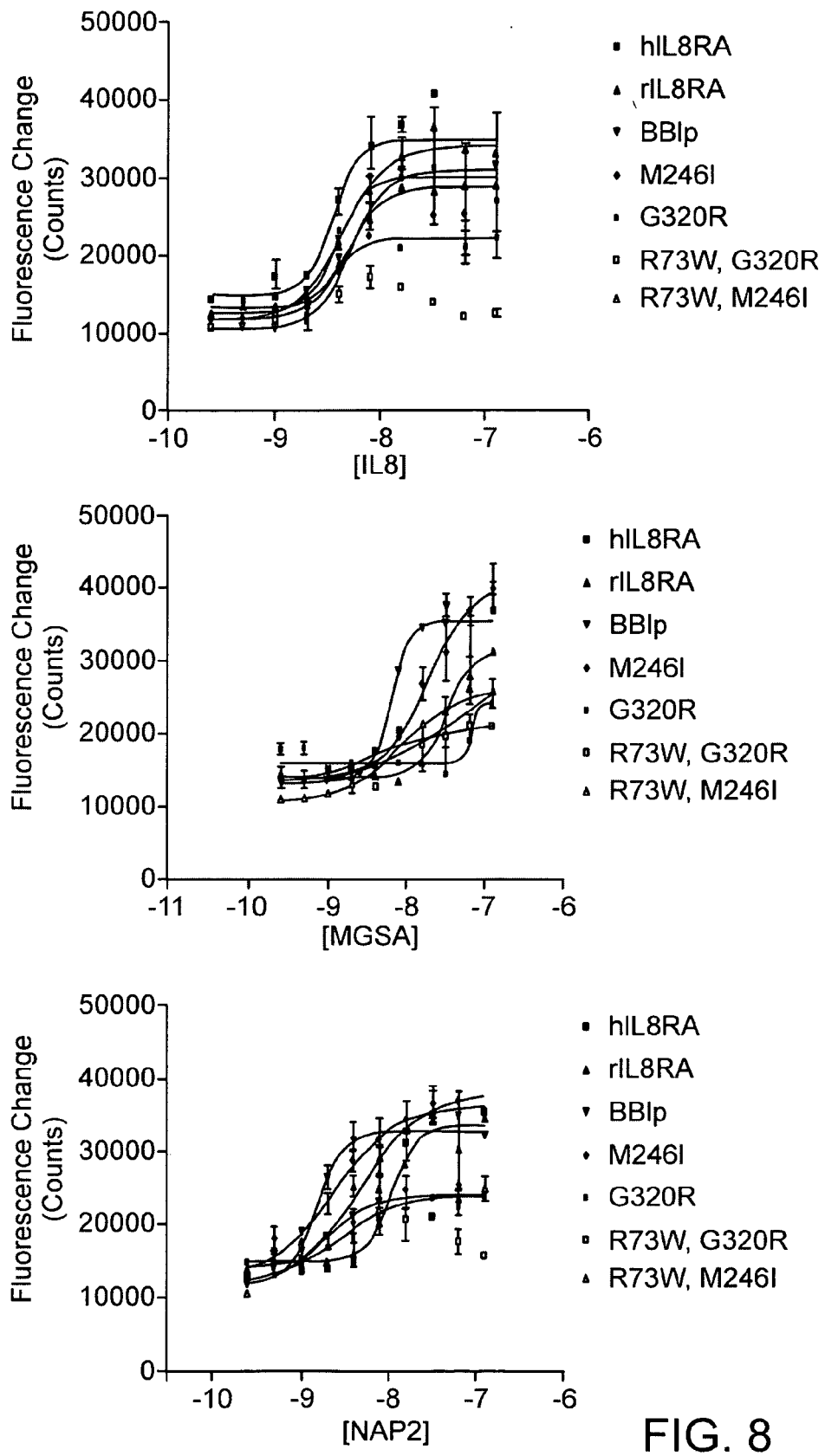
FIG. 8 shows $Ca^{2+}$ flux in mammalian HEK293/Gα16 cells expressing wild type or mutant IL8 receptors.
Figure 9:
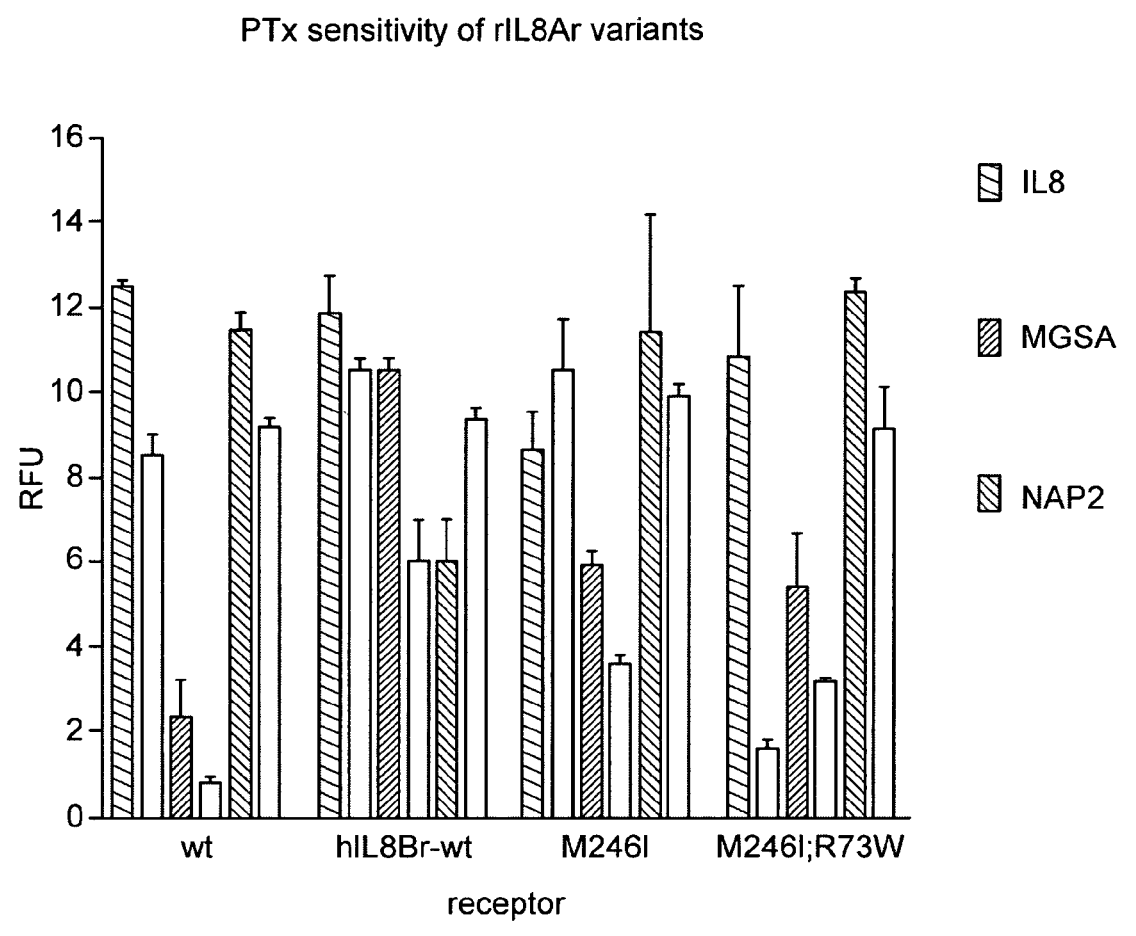

The dose response (FIG. 8) indicates that the M246I mutant recapitulates the novel coupling behavior seen in yeast cells, in that it displays a leftward shift in the MGSA dose response curve, suggesting a higher apparent potency of that agonist on the mutant receptor as compared with wild type. In addition, this mutation in conjunction with the R73W mutation confers a marked sensitivity to pertussis toxin inhibition for IL-8 and to a lesser extent for MGSA/GROα, but not for NAP2 (FIG. 9). These data suggest that these mutations alter the coupling of the IL8 receptor to the G-protein. The mutations may facilitate the ability of a heterologous G-protein to recognize and undergo guanine nucleotide exchange in yeast. Alternatively, it is possible that some of these mutations have affected the binding affinities of the receptor with respect to the various ligands.

EXAMPLE 3

Creation of Mutants of the Galanin Receptor-1

One of the mutations identified in the IL-8 receptor has been transferred to human galanin receptor-1 to enhance signaling by that molecule through Gpa1–Gαi2.

A DNA fragment encoding the human galanin receptor-1 (hGalr1), generated by the PCR primers GLNRPCRF (5'GT-GACTGGTCTGCCATGGAGCTGGCG-GTCGGGAACCT-3') (SEQ ID NO:42) and GLNRPCRR (5'-CGCGGATCCCACATGAGTACAATTGGT-3') (SEQ ID NO:43) from a cloned template (pCR2-hGalr; E. Davis, BMS) was introduced into the yeast expression vector Cp4258 (LEU2 selectable marker, PGK promoter, MFa1 signal and leader sequences) using NcoI and XbaI. The A (R mutation was introduced using the Quik-Change mutagenesis protocol (Stratagene) with the oligonucleotide PX1267 (5'-CTGAAAATT TCAGGAAGAGATATAAACAAGTG TTCAAG-3') (SEQ ID NO:44) and PX1268 (5'-CTTGAACA CTTGTTTATATCTCTTCCTGAAA TTTTCAG) (SEQ ID NO:45).

Oligonucleotides used for PCR cloning from yeast expression vectors were R1CEP4fwd (5'-CCCAAGCT TGCCACCATGGAAGTAAACGTATG-3') (SEQ ID NO:46) and R1CEP4rev (5'-CCCCTCGAGCTA-GAGATTTGAAGGCACGTT-3') (SEQ ID NO:47). The PCR products were cut with HindIII and XhoI and cloned into pCEP4 (Invitrogen) cut with the same enzymes. The clones were sequenced prior to use.

The wild type human galanin receptor-1 couples somewhat weakly to the pheromone response pathway in yeast. In order to improve this response, the amino acid sequences of the rabbit IL8 receptor and the human galanin receptor-1 were compared a region of limited homology in the seventh transmembrane domain and the C-terminal tail was identified. The galanin receptor contains an Ala in the same position as Gly320 of the rabbit IL8 receptor:

LGFLHSCLNPIIYAFIGQNFRN<u>G</u>FLKM rIL8aR (SEQ ID NO: 3)

LAYSNSSVNPIIYAFLSENFRK<u>A</u>YKQV hGalR1 (SEQ ID NO: 5)

Figure 7:
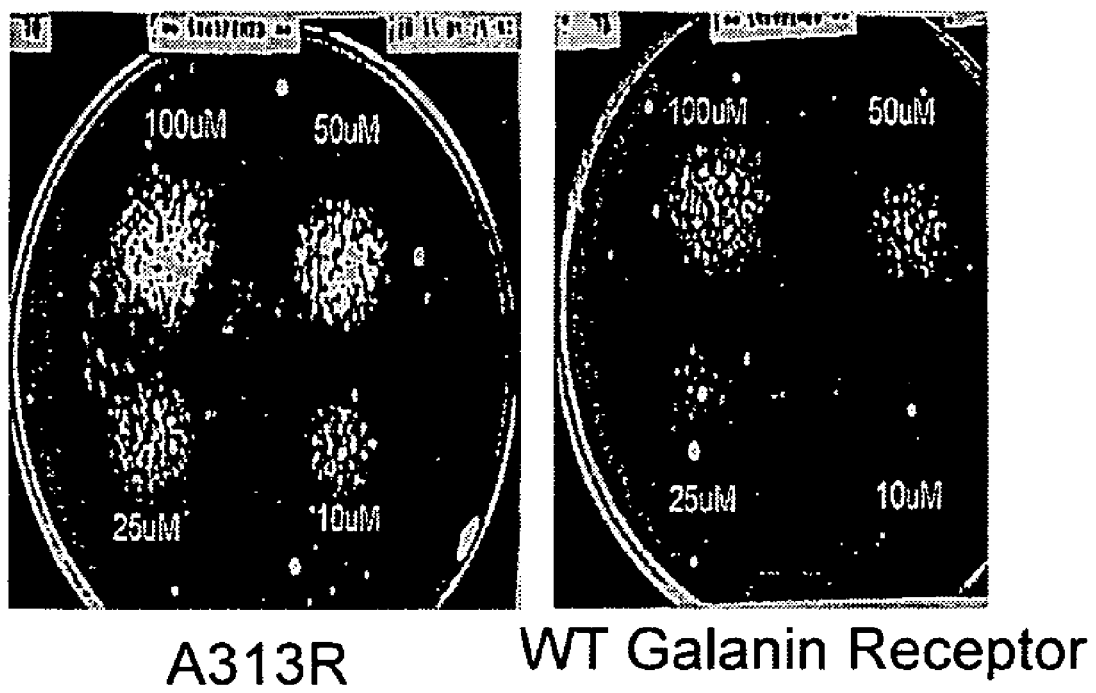
FIG. 7 shows ligand dependent growth of yeast cells expressing wild type or mutant human Galanin receptor.

By changing the Ala (underlined above) to an Arg, the galanin receptor showed an enhanced response to ligand (FIG. 7).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A mutant mammalian IL8A receptor having an amino acid sequence which differs from a wild type IL8A receptor having a wild type amino acid sequence comprising an amino acid motif ($X_1X_2X_3X_4$) proximal to the carboxy terminal end of said wild type amino acid sequence, wherein:
- $X_1$ denotes an amino acid residue at position 1 of said motif and is selected from the group consisting of Phe, Leu, Val, and Tyr;
- $X_2$ denotes an amino acid residue at position 2 of said motif and is selected from the group consisting of Phe, Lys and Gln;
- $X_3$ denotes an amino acid residue at position 3 of said motif and is selected from the group consisting of Leu, Arg, Glu, Asn, Gln, Ser, Ala, Leu; and
- $X_4$ denotes an amino acid residue at position 4 of said motif and is selected from the group consisting of Ala, Cys, Asp, Glu, Gly, Ser, Thr and Tyr; and
- wherein said mutant receptor comprises a seventh transmembrane domain with a carboxy terminal end; and
- at least one amino acid mutation at a position in said amino acid motif, wherein said mutation is selected from the group consisting of: Arg to Trp at position 73, Met to Ile at position 246, and Gly to Arg at position 320, wherein upon interaction with a ligand to modulate a signal transduction pathway in a cell, a signal generated by said mutant receptor is greater than a signal generated upon interaction of said ligand with a wild type IL8A receptor.

2. The receptor of claim 1, wherein said cell is a yeast cell.

3. The receptor of claim 2, wherein said receptor acts as a surrogate for an endogenous yeast pheromone receptor in a pheromone response pathway of said cell.

4. The receptor of claim 2, wherein said cell belongs to the species *Saccharomyces cerevisiae*.

5. The receptor of claim 1, wherein said cell is a mammalian cell.

6. The receptor of claim 1, wherein said mutation comprises mutagenization at position 4 of said amino acid motif to Arg or to Lys.

7. The receptor of claim 1, wherein said ligand is interleukin 8 (IL8) or melanoma growth-stimulating activity-alpha (MGSA/GROα).

8. The mutant mammalian G protein-coupled receptor of claim 1, wherein said amino acid motif commences 5–10 acid residues from the carboxy terminal end of said wild type amino acid sequence.

9. The receptor of claim 1, comprising an amino acid sequence LGFLHSCLNPIIYAFIGQN[FRNG]FLKM (SEQ ID NO:3) wherein said mutant amino acid motif within said sequence is (FRKG) (SEQ ID NO:4).

10. A mutant galanin receptor-1 having an amino acid sequence which differs from a wild type galanin receptor-1 having a wild type amino acid sequence comprising an amino acid motif ($X_1X_2X_3X_4$) proximal to the carboxy terminal end of said wild type amino acid sequence, wherein:
- $X_1$ denotes an amino acid residue at position 1 of said motif and is selected from the group consisting of Phe, Leu, Val, and Tyr;
- $X_2$ denotes an amino acid residue at position 2 of said motif and is selected from the group consisting of Phe, Lys and Gln;
- $X_3$ denotes an amino acid residue at position 3 of said motif and is selected from the group consisting of Leu, Arg, Glu, Asn, Gln, Ser, Ala, Leu; and
- $X_4$ denotes an amino acid residue at position 4 of said motif and is selected from the group consisting of Ala, Cys, Asp, Glu, Gly, Ser, Thr and Tyr; and
- wherein said mutant receptor comprises a seventh transmembrane domain with a carboxy terminal end; and
- at least one amino acid-mutation in said amino acid motif comprising Gly to Ala at position 320, wherein upon interaction with a ligand to modulate a signal transduction pathway in a cell, a signal generated by said mutant receptor is greater than a signal generated upon interaction of said ligand with a wild type galanin receptor-1.

11. The amino acid motif of claim 10, wherein $X_1$ denotes an amino acid residue at position 1 of said motif and is Phe;
- $X_2$ denotes an amino acid residue at position 2 of said motif and is Arg;
- $X_3$ denotes an amino acid residue at position 3 of said motif and is Lys; and
- $X_4$ denotes an amino acid residue at position 4 of said motif and is selected from the group consisting of Ala, Cys, Asp, Glu, Gly, Ser, Thr and Tyr.

12. The receptor of claim 10 or 11, wherein said cell is a yeast cell.

13. The receptor of claim 12, wherein said receptor acts as a surrogate for an endogenous yeast pheromone receptor in a pheromone response pathway of said cell.

14. The receptor of claim 12, wherein said cell belongs to the species *Saccharomyces cerevisiae*.

15. The receptor of claim 10 or 11, wherein said cell is a mammalian cell.

16. The receptor of claim 10 or 11, wherein said receptor comprises mutagenization at position 4 of said amino acid motif to Arg or to Lys.

17. The mutant mammalian G protein-coupled receptor of claim 10, wherein said amino acid motif commences 5–10 amino acid residues from the carboxy terminal end of said wild type amino acid sequence.

18. The receptor of claim 10, comprising an amino acid sequence LAYSNSSVNPIIYAFLSBNI(FRKR)IYKQV (SEQ ID NO:1) wherein said mutant amino acid motif within said sequence is (FRKR) (SEQ ID NO:2).

* * * * *

SEQUENCE LISTING

```
<160> NUMBER OF SEQ ID NOS: 47

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: receptor
      sequence motif
```

```
<400> SEQUENCE: 1

Leu Ala Tyr Ser Asn Ser Ser Val Asn Pro Ile Ile Tyr Ala Phe Leu
 1               5                  10                  15

Ser Glu Asn Phe Arg Lys Arg Tyr Lys Gln Val
             20                  25

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: amino acid
      sequence motif

<400> SEQUENCE: 2

Phe Arg Lys Arg
 1

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: IL-8
      receptor motif

<400> SEQUENCE: 3

Leu Gly Phe Leu His Ser Cys Leu Asn Pro Ile Ile Tyr Ala Phe Ile
 1               5                  10                  15

Gly Gln Asn Phe Arg Asn Gly Phe Leu Lys Met
             20                  25

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: amino acid
      sequence motif

<400> SEQUENCE: 4

Phe Arg Asn Gly
 1

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: galanin
      receptor motif

<400> SEQUENCE: 5

Leu Ala Tyr Ser Asn Ser Ser Val Asn Pro Ile Ile Tyr Ala Phe Leu
 1               5                  10                  15

Ser Glu Asn Phe Arg Lys Ala Tyr Lys Gln Val
             20                  25

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: amino
      terminal domain conserved sequence motif
```

-continued

```
<400> SEQUENCE: 6

Leu Leu Leu Leu Gly Ala Gly Glu Ser Gly
  1               5                  10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: amino
      terminal domain conserved  sequence motif

<400> SEQUENCE: 7

Leu Leu Leu Leu Gly Ala Gly Glu
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: G1 region
      conserved sequence motif

<400> SEQUENCE: 8

Gly Ser Gly Glu Ser Gly Asp Ser Thr
  1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: GPA1 amino
      terminal sequence motif

<400> SEQUENCE: 9

Gln Ala Arg Lys Leu Gly Ile Gln
  1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: G alpha
      conserved  sequence motif

<400> SEQUENCE: 10

Asp Val Gly Gly Gln
  1               5

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
cccccatgga agtaaacgta tggaatatg                                       29

<210> SEQ ID NO 12
<211> LENGTH: 27
<212> TYPE: DNA
```

```
<213> ORGANISM: Artificial Sequence
<220> FEATURE:
<223> OTHER INFORMATION: Description of Artificial Sequence:
      oligonucleotide primer

<400> SEQUENCE: 12
ccctctagag atttgaaggc acgttgg                                           27

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: IL-8 fusion
      junction

<400> SEQUENCE: 13

Leu Lys Arg Ser Ala Lys Glu Leu Arg Cys Gln Cys Ile
 1               5                  10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: MGSA fusion
      junction

<400> SEQUENCE: 14

Leu Lys Arg Ala Ser Val Ala Thr Glu Leu Arg Cys Gln Cys Leu
 1               5                  10                  15

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: NAP2 fusion
      junction

<400> SEQUENCE: 15

Leu Lys Arg Ala Glu Leu Arg Cys Met Cys Ile
 1               5                  10

<210> SEQ ID NO 16
<211> LENGTH: 57
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
ttaagcgtga ggcagaagct tctgctaagg aattgagatg tcaatgtatt aagactt        57

<210> SEQ ID NO 17
<211> LENGTH: 59
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
actctaagcc attccatcca aagttcatta aggaattgag agttattgaa tctggtcca      59

<210> SEQ ID NO 18
```

```
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
cattgtgcta acactgaaat tattgttaag ttgtctgatg gtagagaatt gtgtttggat      60

<210> SEQ ID NO 19
<211> LENGTH: 63
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
ccaaaggaaa actgggttca aagagttgtt gaaaagttct tgaagagagc tgaaaactct      60
tga                                                                    63

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
tagagtaagt cttaatacat tgacatctca attccttagc agaagcttct gcctcacgc       59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
acaatgtgga ccagattcaa taactctcaa ttccttaatg aactttggat ggaatggct       59

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
ctttggatcc aaacacaatt ctctaccatc agacaactta acaataattt cagtgttagc      60

<210> SEQ ID NO 23
<211> LENGTH: 61
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
gatctcaaga gttttcagct ctcttcaaga acttttcaac aactctttga acccagtttt      60
c                                                                      61
```

```
<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 24
ccgcttaagc gttctgctaa ggaattgaga tgtc                          34

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 25
aagtatattg tattttgtac gagc                                     24

<210> SEQ ID NO 26
<211> LENGTH: 56
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
ttaagcgtgc gtccgttgct acagaattga ggtgtcaatg tctacaaact ttgcaa   56

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
ggtatccacc caaagaacat tcagtcagtt aacgttaagt ccccaggtcc acactgtgc  59

<210> SEQ ID NO 28
<211> LENGTH: 57
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
tcagactgaa gtcatagcta cattaaagaa tggtcgtaaa gcctgtttaa atcctgc   57

<210> SEQ ID NO 29
<211> LENGTH: 58
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
atccccaata gtaaagaaaa tcatcgaaaa gatgttgaat agtgataaat ccaattaa  58
```

<210> SEQ ID NO 30
<211> LENGTH: 58
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
gatcttaatt ggatttatca ctattcaaca tcttttcgat gattttcttt actattgg       58

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
ggatgcagga tttaaacagg ctttacgacc attctttaat gtagctatga cttcagt        57

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
ctgagcacag tgtggacctg gggacttaac gttaactgac tgaatgttct ttgggtgga      59

<210> SEQ ID NO 33
<211> LENGTH: 56
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
taccttgcaa agtttgtaga cattgacacc tcaattctgt agcaacggac gcacgc         56

<210> SEQ ID NO 34
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
ttaagcgtgc tgaattgaga tgtatgtgta tcaagaccac ctctggtatc caccc          55

<210> SEQ ID NO 35
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
aaagaacatc caatctttgg aagttatcgg taagggtact cactgtaacc aagtt          55

```
<210> SEQ ID NO 36
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
gaagttatcg ctaccttgaa ggacggtaga aagatttgtt tggacccaga cgctc          55

<210> SEQ ID NO 37
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
caagaatcaa gaagatcgtt caaaagaagt tggctggtga cgaatctgct gacta          55

<210> SEQ ID NO 38
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
gatctagtca gcagattcgt caccagccaa cttcttttga acgatcttct tgatt          55

<210> SEQ ID NO 39
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
cttggagcgt ctgggtccaa acaaatcttt ctaccgtcct tcaaggtagc gataa          55

<210> SEQ ID NO 40
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
cttcaacttg gttacagtga gtacccttac cgataacttc caaagattgg atgtt          55

<210> SEQ ID NO 41
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
ctttgggtgg ataccagagg tggtcttgat acacatacat ctcaattcag cacgc          55

<210> SEQ ID NO 42
```

<211> LENGTH: 37
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 42
gtgactggtc tgccatggag ctggcggtcg ggaacct                    37

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 43
cgcggatccc acatgagtac aattggt                              27

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 44
ctgaaaattt caggaagaga tataaacaag tgttcaag                  38

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 45
cttgaacact tgtttatatc tcttcctgaa attttcag                  38

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 46
cccaagcttg ccaccatgga agtaaacgta tg                        32

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 47
cccctcgagc tagagatttg aaggcacgtt                           30